(12) United States Patent
Papadopoulos et al.

(10) Patent No.: US 7,267,977 B2
(45) Date of Patent: Sep. 11, 2007

(54) PERIPHERAL-TYPE BENZODIAZEPINE RECEPTOR: A TOOL FOR DETECTION, DIAGNOSIS, PROGNOSIS, AND TREATMENT OF CANCER

(75) Inventors: Vassilios Papadopoulos, North Potomac, MD (US); Martine Culty, North Potomac, MD (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 09/047,652

(22) Filed: Mar. 25, 1998

(65) Prior Publication Data

US 2003/0157095 A1 Aug. 21, 2003

(51) Int. Cl.
*C12M 15/63* (2006.01)
(52) U.S. Cl. ............... 435/320.1; 435/252.3; 435/69.1; 536/23.1; 536/24.5; 514/44
(58) Field of Classification Search ........... 530/300, 530/387.1; 424/130.1; 514/2
See application file for complete search history.

(56) References Cited

U.S. PATENT DOCUMENTS

| | | | |
|---|---|---|---|
| 5,350,836 A | | 9/1994 | Kopchick et al. |
| 5,407,799 A | * | 4/1995 | Studier ............ 435/6 |
| 5,585,479 A | * | 12/1996 | Hoke et al. ........ 536/24.5 |
| 5,663,062 A | * | 9/1997 | Sorge et al. ........ 435/91.1 |
| 5,840,708 A | * | 11/1998 | Weiss ............ 514/44 |
| 5,948,676 A | | 9/1999 | Chang et al. |
| 2003/0157095 A1 | | 8/2003 | Papadopoulos |
| 2006/0106202 A1 | | 5/2006 | Papadopoulos et al. |

FOREIGN PATENT DOCUMENTS

| | | | |
|---|---|---|---|
| WO | WO-9949316 A2 | 9/1999 | |
| WO | WO-0001821 A2 | 1/2000 | |
| WO | WO-0009549 A2 | 2/2000 | |

OTHER PUBLICATIONS

Mosser, PC. Drug Devel. Res. 30(4): 213-218, 1993.*
Garnier, M. Endocrinology. 132(1): 444-458, 1993.*
Papadoponlosis, V. JBC. 272: 32129-32135, 1997.*
Branch, AD. TIBS 23 : 45-50, 1998.*
Casalotti, SO, gene 121 (2) 377-382, 1992.*
Lu C, Clin. Camier Res. 2(8): 1417-25, 1996.*
MPSRCH search report, 1998, us-09-047-652A-1.rge, p. 1-2, and us-09-047-652A-2.rge, p. 1-2.*
Papadopoulous, 1997, JBC, 272: 32129-32135.*
Harris et al. J. of The Am Society of Nephrology 6:1125-33, 1995.*
Ahn et al. Nature Genetics 3(4):283-91, 1993.*
Cawthon et al. Genomics 9(3):446-60, 1991.*
Drexler et al, 1993 (Leukemia and Lymphoma, 9:1-25).*
Embleton et al, 1984 (Immunol Ser, 23:181-207).*
Hsu, 1973 (in Tissue Culture Methods and Applications, Kruse and Patterson, Eds, Academic Press, NY, see abstract, p. 764-767.*
Tian, J et al, 2004 (Physiol Genomics, 17: 170-182).*
Van Dyke D L et al, 2003 (Cancer Genetics and Cytogenetics 241: 137-141).*
Zaslav A L et al, 2002 (Amer J Medical Genetics 107: 174-176).*
Kunkel, P, et al, 2001 (Neuro-oncology 3(2): 82-88).*
Ellis et al., J Biol Chem. Jan. 9, 1998;273(2):1052-7, Abstract only.
Resnicoff et al., Cancer Immunol Immunother. Jan. 1996;42(1):64-8, Abstract only.
Rutka et al., Cancer Res. Jun. 15, 1994;54(12):3267-72, Abstract only.
Waki et al., Biochem Biophys Res Commun. Jun. 15, 1994;201(2):1001-7, Abstract only.
"International Search Report in PCT/US99/18507", (Jun. 15, 2000),7 Pages.
"International Search Report in PCT/US 99/05853", 5 Pages.
Boyle, T P., et al., "Structure of the murine gene encoding apolipoprotein A-I.", *Gene*, 117(2), (Aug. 15, 1992),243-7.
Don, J , et al., "Identification and characterization of the regulated pattern of expression of a novel mouse gene, meg1, during the meiotic cell cycle", *Cell Growth Differ.*, 3(8), (Aug. 1992),495-505.
Don, J. , "M. musculus mRNA meg1", *Database EMBL [Online] AC X64455*, (Feb. 21, 1992),2 Pages.
Ever, L , et al., "Two alternatively spliced Meig1 messenger RNA species are differentially expressed in the somatic and in the germ-cell compartments of the testis", *Cell Growth Differ.*, 10(1), (Jan. 1999),19-26.
Farges, R , et al., "Site-directed mutagenesis of the peripheral benzodiazepine receptor: identification of amino acids implicated in the binding site of Ro5-4864", *Mol. Pharmacol.*, 46(6), (Dec. 1994),1160-7.
Galiegue, S. , et al., "Cloning and Characterization of PRAX-1—A New Protein that Specifically Interacts with the Peripheral Benzodiazepine Receptor", *The Journal of Biological Chemistry*, 274(5), (Jan. 29, 1999),2938-2952.
Glenney, J R., et al., "The sequence of human caveolin reveals identity with VIP21, a component of transport vesicles.", *FEBS Letters*, 314(1), (Dec. 7, 1992),45-48.
Hardwick, M. , et al., "Abstract #1569 The Peripheral-type Benzodiazepine Receptor in Human Breast Cancer", *Proceedings of the American Association for Cancer Research*, 38, (Apr. 1997),233.

(Continued)

Primary Examiner—Shanon Foley
Assistant Examiner—Minh-Tam Davis
(74) Attorney, Agent, or Firm—Schwegman, Lundberg, Woessner & Kluth P.A.

(57) ABSTRACT

The expression and subcellular localization of peripheral-type benzodiazepine receptors (PBR) is shown in this application to correlate with the metastatic potential of cells, and increased cell proliferation. Inhibition of PBR expression, function or stability results in a decrease in cell proliferation. Compositions and methods for regulating and/or monitoring PBR and its expression are useful for the detection, diagnosis, prognosis and treatment of solid tumors, in particular, breast cancer.

13 Claims, 13 Drawing Sheets

OTHER PUBLICATIONS

Hardwick, M., et al., "Perpheral-Type Benzodiazepine Receptor (PBR) in Human Breast Cancer: Correlation of Breast Cancer Cell Aggressive Phenotype with PBR Expression, Nuclear Localization, and PBR-mediated Cell Proliferation and Nuclear Transport of Cholesterol", *Cancer Research*, 59(4), (1999),831-842.

Kozikowski, A. P., et al., "Synthesis and Biology of a 7-Nitro-2,1,3-benzoxadiazol-4-yl Derivative of 2-Phenylindole-3-acetamide: A Fluorescent Probe for the Peripheral-Type Benzodiazepine Receptor", *Journal of Medicinal Chemistry*, 40(16), (1997),2435-2439.

Krueger, K. E., et al., "Peripheral-type Benzodiazepine Receptors Mediate Translocation of Cholesterol from Outer to Inner Mitochondrial Membranes in Adrenocortical Cells", *The Journal of Biological Chemistry*, 265(25), (1990),15015-15022.

Li, Hua, et al., "Identification, Localization, and Function in Steroidogenesis of PAP7: A Peripheral-Type Benzodiazepine Receptor- and PKA (RI?Ñ)-Associated Protein", *Molecular Endocrinology 15*(12), (2001),2211-2228.

Li, H., et al., "M. musculus peripheral benzodiazepine receptor associated protein", *Database EMBL [Online] AC AF022770*, (Oct. 1, 1997),1 page.

Li, H., et al., "Peripheral-type benzodiazepine receptor function in cholesterol transport. Identification of a putative cholesterol recognition/interaction amino acid sequence and consensus pattern", *Endocrinology*, 139(12), (1999),4991-4997.

Marra, M., et al., "mo98e12.r1 Stratagene mouse testis (#937308) Mus musculus cDNA clone", *Database EMBL [Online] AC AA174581*, (Dec. 31, 1996),2 Pages.

Miettinen, H., et al., "Expression of peripheral-type benzodiazepine receptor and diazepam binding inhibitor in human astrocytomas: relationship to cell proliferation", *Cancer Research*, 55(12), (Jun. 15, 1995),2691-5.

Papadopoulos, V., et al., "Cholesterol Recognition Sequence", U.S. Appl. No. 09/623,922, filed Sep. 11, 2000.

Papadopoulos, V., et al., "Peripheral-Type Benzodiazepine Receptor: a Tool for Detection, Diagnosis, Prognosis, and Treatment of Cancer", U.S. Appl. No. 09/646,932, filed Sep. 25, 2000.

Papadopoulos, V, "Structure and function of the peripheral-type benzodiazepine receptor in steroidogenic cells", *Proceedings of the Society for Experimental Biology & Medicine*, 217(2), (Feb. 2, 1998),130-142.

Pawlikowski, M., et al., "Inhibition of Cell Proliferation of Human Gliomas by Benzodiazepines in vitro", *Acta Neurol Scand.*, 77, (1988),231-233.

Pikuleva, Irina A., et al., "Active-site topology of bovine cholestrol side-chain cleavage cytochrome P450 (P450scc) and evidence for interaction of tyrosine 94 with the side chain of cholesterol", *Archives of Biochemistry and Biophysics*, 322(1), (Sep. 10, 1995),189-97.

Riond, J., et al., "Molecular cloning and chromosomal localization of a human peripheral-type benzodiazepine receptor", *European Journal of Biochemistry*, 195(2), (Jan. 1991),305-311.

Sambrook, J., et al., "Molecular Cloning—a Laborary Manual", *2d Edition, Cold Spring Laboratory Press*, (1989),9.47-9.62.

Sher, I, et al., "Mutations uncouple human fibroblast growth factor (FGF)-7 biological activity and receptor binding and support broad specificity in the secondary receptor binding site of FGFs.", *Journal of Biological Chemistry*, 274(49), (Dec. 3, 1999),35016-35022.

Su, P, et al., "A cDNA encoding a rat mitochondrial cytochrome P450 catalyzing both the 26-hydroxylation of vitamin D3: gonadotropic regulation of the cognate mRNA in ovaries", *DNA and Cell Biology 9*(9), (Nov. 1990),657-67.

Yakovlev, et al., "GenBank TM Database Entry", Accession No. U12421, (1995).

Liu, Jun, et al., "Molecular cloning, chromosomal localization of human peripheral-type benzodiazepine receptor- and protein kinase A regulatory subunit type 1A (PRKAR1A)-associated protein PAP7 and studies in PRKAR1A mutant cells and tissues", *The FASEB Journal, express article 10.1096/fj.02-1066fje*, (Apr. 8, 2003),27 pgs.

Papadopoulos, Vassilios, et al., "The Peripheral-type Benzodiazepine Receptor Is Functionally Linked to Leydig Cell Steroidogenesis", *Journal of Biological Chemistry 265*(7), (Mar. 5, 1990),3772-3779.

* cited by examiner

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 652 base pairs
       (B) TYPE: Nucleic acid
       (C) STRANDEDNESS: Single
       (D) TOPOLOGY: Linear (ii) SEQUENCE DESCRIPTION: SEQ ID NO:1:

```
CCACGGCGAA GGTCTCCGCT GGTACGCCGG CCTGCAGAAG                    40

CCCTCGTGGC ACCCGCCCCA CTGGGTGCTG GGCCCTGTCT                    80

GGGGCACGCT CTACTCAGCC ATGGGTACG GCTCCTACCT                    120

GGTCTGGAAA GAGCTGGGAG GCTTCACAGA GAAGGCTGTG                   160

GTTCCCCTGG GCCTCTACAC TGGGCAGCTG GCCCTGAACT                   200

GGGCATGGCC CCCCATCTTC TTTGGTGCCC GACAAATGGG                   240

CTGGGCCTTG GTGGATCTCC TGCTGGTCAG TGGGGCGGCG                   280

GCAGCCACTA CCGTGGCCTG GTACCAGGTG AGCCCGCTGG                   320

CCGCCCGCCT GCTCTACCCC TACCTGGCCT GGCTGGCCTT                   360

CACGACCACA CTCAACTACT GCGTATGGCG GGACAACCAT                   400

GGCTGGCGTG GGGACGGCG GCTGCCAGAG TGAGTGCCCG                    440

GCCCACCAGG GACTGCAGCT GCACCAGCAG GTGCCATCAC                   480

GCTTGTGATG TGGTGGCCGT CACGCTTTCA TGACCACTGG                   520

GCCTGCTAGT CTGTCAGGGC CTTGGCCCAG GGGTCAGCAG                   560

AGCTTCAGAG GTGGCCCCAC CTGAGCCCCC ACCCGGGAGC                   600

AGTGTCCTGT GCTTTCTGCA TGCTTAGAGC ATGTTCTTGG                   640

AACATGGAAT TT                                                 652
```

(2) INFORMATION FOR SEQ ID NO:2:

(i) SEQUENCE CHARACTERISTICS:
       (A) LENGTH: 652 base pairs
       (B) TYPE: Nucleic acid
       (C) STRANDEDNESS: Single
       (D) TOPOLOGY: Linear (ii) SEQUENCE DESCRIPTION: SEQ ID NO:2:

```
CCACGGCGAG GGTCTCCGCT GGTACGCCGG CCTGCAGAAG                    40

CCCTCGTGGC ACCCGCCCCA CTGGGTGCTG GGCCCTGTCT                    80

GGGGCACGCT CTACTCAGCC ATGGGGTACG GCTCCTACCT                   120

GGTCTGGAAA GAGCTGGGAG GCTTCACAGA GAAGGCTGTG                   160

GTTCCCCTGG GCCTCTACAC TGGGCAGCTG GCCCTGAACT                   200

GGGCATGGCC CCCCATCTTC TTTGGTGCCC GACAAATGGG                   240

CTGGGCCTTG GTGGATCTCC TGCTGGTCAG TGGGGCGGCG                   280

GCAGCCACTA CCGTGGCCTG GTACCAGGTG AGCCCGCTGG                   320
```

```
CCGCCCGCCT GCTCTACCCC TACCTGGCCT GGCTGGCCTT          360

CACGACCACA CTCAACTACT GCGTATGGCG GGACAACCAT          400

GGCTGGCGTG GGGGACGGCG GCTGCCAGAG TGAGTGCCCG          440

GCCCACCAGG GACTGCAGCT GCACCAGCAG GTGCCATCAC          480

GCTTGTGATG TGGTGGCCGT CACGCTTTCA TGACCACTGG          520

GCCTGCTAGT CTGTCAGGGC CTTGGCCCAG GGGTCAGCAG          560

AGCTTCAGAG GTGGCCCCAC CTGAGCCCCC ACCCGGGAGC          600

AGTGTCCTGT GCTTTCTGCA TGCTTAGAGC ATGTTCTTGG          640

AACATGGAAT TT                                        652
```

(2) INFORMATION FOR SEQ ID NO:3:

(i) SEQUENCE CHARACTERISTICS:
        (A) LENGTH: 169 amino acids
        (B) TYPE: amino acid
        (D) TOPOLOGY: Linear (ii) SEQUENCE DESCRIPTION: SEQ ID NO:3:

```
Xaa Xaa Xaa Xaa Xaa Xaa Xaa Xaa Xaa Xaa
 1               5                  10

Xaa Xaa Xaa Xaa Xaa Xaa Xaa Xaa Xaa Xaa
            15                      20

Xaa Xaa Xaa Xaa Xaa Xaa His Gly Glu Gly
        25                          30

Leu Arg Trp Tyr Ala Gly Leu Gln Lys Pro
        35                          40

Ser Trp His Pro Pro His Trp Val Leu Gly
        45                          50

Pro Val Trp Gly Thr Leu Tyr Ser Ala Met
        55                          60

Gly Tyr Gly Ser Tyr Leu Val Trp Lys Glu
        65                          70

Leu Gly Gly Phe Thr Glu Lys Ala Val Val
        75                          80

Pro Leu Gly Leu Tyr Thr Gly Gln Leu Ala
        85                          90

Leu Asn Trp Ala Trp Pro Pro Ile Phe Phe
        95                          100

Gly Ala Arg Gln Met Gly Trp Ala Leu Val
        105                         110

Asp Leu Leu Leu Val Ser Gly Ala Ala Ala
        115                         120

Ala Thr Thr Val Ala Trp Tyr Gln Val Ser
        125                         130

Pro Leu Ala Ala Arg Leu Leu Tyr Pro Tyr
        135                         140

Leu Ala Trp Leu Ala Phe Thr Thr Thr Leu
        145                         150

Asn Tyr Cys Val Trp Arg Asp Asn His Gly
        155                         160

Trp Arg Gly Gly Arg Arg Leu Pro Glu
        165
```

PERIPHERAL-TYPE BENZODIAZEPINE RECEPTOR: A TOOL FOR DETECTION, DIAGNOSIS, PROGNOSIS, AND TREATMENT OF CANCER

STATEMENT OF GOVERNMENT RIGHTS

The invention was made, at least in part, with a grant from the Government of the United States of America (grant ES-07447 from the National Institutes of Health). The Government may have certain rights in the invention.

INTRODUCTION

Tumor progression is a multi-step process in which normal cells gradually acquire more malignant phenotypes, including the ability to invade tissues and form metastases, the primary cause of mortality in breast cancer. During this process, the "aberrant" expression of a number of gene products may be the cause or the result of tumorigenesis. Considering that the first step of tumor progression is cell proliferation, it can be proposed that tumorigenesis and malignancy are related to the proliferative potential of tumoral cells.

Studies in a number of tumors such as rat brain containing glioma tumors [Richfield, E. K. et al. (1988) *Neurology* 38:1255-1262], colonic adenocarcinoma and ovarian carcinoma [Katz, Y. et al. (1988) *Eur. J. Pharmacol.* 148: 483-484 and Katz, Y. et al. (1990) *Clinical Sci.* 78:155-158] have shown an abundance of peripheral-type benzodiazepine receptors (PBR) compared to normal tissue. All documents cited herein infra and supra are hereby incorporated in their entirety by reference thereto. Moreover, a 12-fold increase in PBR density relative to normal parenchyma, was found in human brain glioma or astrocytoma [Cornu, P. et al. (1992) *Acta Neurochir.* 119:146-152]. The authors suggested that PBR densities may reflect the proliferative activity of the receptor in these tissues. Recently, the involvement of PBR in cell proliferation was further shown [Neary, J. T. et al. (1995) *Brain Research* 675:27-30; Miettinen, H. et al. (1995) *Cancer Research* 55:2691-2695], and its expression in human astrocytic tumors was found to be associated with tumor malignancey and proliferative index [Miettinen, H. et al. supra; Alho, H. (1994) *Cell Growth Different.* 5:1005-1014].

PBR is an 18-kDa protein discovered as a class of binding sites for benzodiazepines distinct from the GABA neurotransmitter receptor (Papadopoulos, V. (1993) *Endocr. Rev.* 14:222-240]. PBR are extremely abundant in steroidogenic cells and found primarily on outer mitochondrial membranes [Anholt, R. et al. (1986) *J. Biol. Chem.* 261: 576-583]. PBR is thought to be associated with a multimeric complex composed of the 18-kDa isoquinoline-binding protein and the 34-kDa pore-forming voltage-dependent anion channel protein, preferentially located on the outer/inner mitochondrial membrane contact sites [McEnery, M. W. et al. *Proc. Natl. Acad. Sci. U.S.A.* 89:3170-3174; Garnier, M. et al. (1994) *Mol. Pharmacol.* 45:201-211; Papadopoulos, V. et al. (1994) *Mol. Cel. Endocr.* 104:R5-R9]. Drug ligands of PBR, upon binding to the receptor, simulate steroid synthesis in steroidogenic cells in vitro [Papadopoulos, V. et al. (1990) *J. Biol. Chem.* 265:3772-3779; Ritta, M. N. et al. (1989) *Neuroendocrinology* 49: 262-266; Barnea, E. R. et al. (1989) *Mol. Cell. Endocr.* 64:155-159; Amsterdam, A. and Suh, B. S. (1991) *Endocrinology* 128:503-510; Yanagibashi, K. et al. (1989) *J. Biochem.* (Tokyo) 106: 1026-1029]. Likewise, in vivo studies showed that high affinity PBR ligands increase steroid plasma levels in hypophysectomized rats [Amri, H. et al. (1996) *Endocrinology* 137:5707-5718]. Further in vitro studies on isolated mitochondria provided evidence that PBR ligands, drug ligands, or the endogenous PBR ligand, the polypeptide diazepam-binding inhibitor (BDI) [Papadopoulos, V. et al. (1997) *Steroids* 62:21-28], stimulate pregnenolone formation by increasing the rate of cholesterol transfer from the outer to the inner mitochondrial membrane [Krueger, K. E. and Papadopoulos, V. (1990) *J. Biol. Chem.* 265:15015-15022; Yanagibashi, K. et al. (1988) *Endocrinology* 123: 2075-2082; Besman, M. J. et al. (1989) *Proc. Natl. Acad. Sci. U.S.A.* 86: 4897-4901; Papadopoulos, V. et al. (1991) *Endocrinology* 129: 1481-1488].

Based on the amino acid sequence of the 18-kDa PBR, a three dimensional model was developed [Papadopoulos, V. (1996) In: The Leydig Cell. Payne, A. H. et al. (eds) Cache River Press, IL, pp 596-628]. This model was shown to accomodate a cholesterol molecule and function as a channel, supporting the role of PBR in cholesterol transport. Recently we demonstrated the role of PBR in steroidogenesis by generating PBR negative cells by homologous recombination [Papadopoulos, V. et al. (1997) *J. Biol. Chem.* 272:32129-32135] that failed to produce steroids. However, addition of the hydrosoluble analogue of cholesterol, 22R-hydroxycholesterol, recovered steroid production by these cells, indicating that the cholesterol transport mechanism was impaired. Further cholesterol transport experiments in bacteria expressing the 18-kDa PBR protein provided definitive evidence for a function as a cholesterol channel/transporter [Papadopoulos, V. et al. (1997) supra].

Diazepam has been shown to induce murine Friend erythroleukemia cell differentiation and inhibit 3T3 cell proliferation. Moreover, benzodiazepines (BZs) inhibited thymoma cell proliferation at micromolar concentrations [Clarke, G. D. and Ryan, P. J. (1980) *Nature* 287:160-161; Wang, J. K. T. et al. (1984) *Proc. Natl. Acad. Sci. U.S.A.* 81: 753-756]. Since the cells used do not express GABA receptor, these studies supported an effect by BZs on cell proliferation acting through a GABA receptor-independent mechanism. Then stimulation of glioma, astrocytoma, and V79 Chinese Hamster lung cell proliferation was shown to occur with treatment with nanomolar concentrations of PBR ligands Ro5-4864 or PK11195, while micromolar amounts of these compounds inhibited proliferation [Ikezaki, K. and Black K. L. (1990) *Cancer Letters* 49:115-120; Bruce, J. H. et al. (1991) *Brain Research* 564: 167-170; Camins, A. et al. (1995) *Eur. J. Pharm.* 272:289-292]. The use of PK11195 (an exclusive PBR ligand) provided unequivocal evidence that the effects seen were mediated by PBR. In addition, micromolar amount of PBR ligands were shown to inhibit growth factor-induced cell proliferation in both astrocytes and lymphoma cells [Laird II, H. E. et al. (1989) *Eur. J. Pharm.* 171:25-35; Neary, J. T. et al. (1995) *Brain Research* 675:27-30].

We hypothesized that the peripheral-type benzodiazepine receptor is part of the changes in cellular and molecular functions that account for the increased aggressive behavior in cancer, and we chose to examine this hypothesis in human breast cancer. Breast cancer is the most common neoplasm and the leading cause of cancer-related deaths for women in most developing countries [Lippman, M. E. (1993) *Science* 259:631-632], affecting nearly 184,000 women, with over 46,000 deaths annually in the U.S. alone (American Cancer Society, 1996). Human breast cells are unlike brain and gonadal cells and cannot produce steroids, but like many other cells in the body, are able to metabolize steroids. Initial results indicated that invasive and non-aggressive human breast cancer cell lines most commonly used for modeling human breast cancer bound the PBR-specific ligand to amounts similar to normal breast tissue. Only when aggressive breast cancer cell lines were assayed was a dramatic increase in PBR binding relative to invasive but non-aggressive cell lines evident. Applicants believe that involvement of PBR in aggressive human breast cancer was not previously discovered because these aggressive cell lines are not the standard cell lines used for studying aberrant behavior in human breast cancer.

In view of these initial results using aggressive human breast cancer cell lines, further characterization of PBR in human breast cancer biopsies, led to the discovery that the invasive and metastatic ability of human breast tumor cells is proportional to the level of PBR expressed, and correlates with the subcellular localization of PBR in these cells in that PBR is found primarily in the nucleus in aggressive tumor cells whereas PBR is found primarily in the cytoplasm of invasive but non-aggressive cells. These changes in PBR expression can be used as a tool for detection, diagnosis, prevention and treatment in breast cancer patients, in particular, and in aggressive solid tumors in general.

SUMMARY OF THE INVENTION

In this application is described a novel cellular and molecular indicator for the detection, diagnosis, treatment and prognosis of aggressive tumors, in particular, breast cancer.

We used a battery of breast cancer cell lines that differ in their invasive and metastatic abilities in order to determine whether PBR expression correlates with the metastatic potential of these cells. In addition, we used biopsies from normal breast tissue and metastatic breast tumors to study PBR expression. Our results demonstrate that the expression of PBR correlates with the expression of breast cancer cell aggressive phenotype. In addition, and in agreement with the well documented function of PBR in steroid synthesizing tissues, cholesterol transport into mitochondria, the function identified in aggressive breast tumor cells is cholesterol uptake by the nucleus which may lead to increased cell proliferation and metastasis. Moreover, inhibition of the expression of the receptor in tumor cells, using targeted disruption of the PBR gene, resulted in a decrease in cell proliferation.

Therefore, it is a purpose of this invention to provide a method for detecting the level of metastatic ability of cells by measuring the level of peripheral benzodiazepine receptors (PBR) in tumor cells and comparing it to the level of PBR in normal cells. This method is applicable to any solid tumor cells, in particular, breast cancer cells, cells from gonadal tumors, and cells from brain tumors.

It is a further object of the invention to provide a composition effective for detecting peripheral-type benzodiazepine receptors such as an anti-PBR antibody or a natural or synthetic ligand of PBR including natural ligands, meaning ligands derived from a natural source such as a plant extract or ligands naturally present in the body or cell, or synthetic ligands such as chemically synthesized ligands or synthesized derivatives of natural ligands of PBR for prognosis of breast cancer, monitoring response to anticancer therapy, and detecting recurrence of metastatic breast cancer.

It is another purpose of the present invention to provide a method for determining the phenotype of a tumor by detecting the location of PBR in cells whereby localization of PBR in the cytoplasm indicates a non-aggressive phenotype and localization of PBR in the nucleus indicates an aggressive phenotype.

It is a further object of the present invention to provide a diagnostic kit comprising ligands or antibodies suitable for detecting PBR and ancillary reagents required for such a detection.

It is yet another object of the present invention to provide a method for detecting the level of PBR in tumor cells using the polymerase chain reaction said method comprising:
    (i) extracting RNA from a sample;
    (ii) reverse transcribing said RNA into cDNA
    (ii) contacting said cDNA with
        (a) at least four nucleotide triphosphates,
        (b) a primer that hybridizes to PBR cDNA, and
        (c) an enzyme with polynucleotide synthetic activity,
    under conditions suitable for the hybridization and extension of said first primer by said enzyme, whereby a first DNA product is synthesized with said DNA as a template therefor, such that a duplex molecule is formed;
    (iii) denaturing said duplex to release said first DNA product from said DNA;
    (iv) contacting said first DNA product with a reaction mixture comprising:
        (a) at least four nucleotide triphosphates,
        (b) a second primer that hybridizes to said first DNA, and
        (c) an enzyme with polynucleotide synthetic activity,
    under conditions suitable for the hybridization and extension of said second primer by said enzyme, whereby a second DNA product is synthesized with said first DNA as a template therefor, such that a duplex molecule is formed;
    (v) denaturing said second DNA product from said first DNA product;
    (vi) repeating steps iii-vi for a sufficient number of times to achieve linear production of said first and second DNA products;
    (vii) fractionating said first and second DNA products generated from said PBR cDNA; and
    (viii) comparing the level of PBR cDNA with the level of PBR cDNA from a normal cell;

wherein, an increase in PBR level over normal cells indicates the progression of the tumor cell to an aggressive phenotype.

It is yet another object of the present invention to provide a composition suitable for detecting the level of PBR RNA in a cell, such as oligonucleotide probes specific for PBR cDNA or RNA for use in methods to detect PBR expression such as in situ hybridization of tissue samples, or northern hybridization assays, or PCR assays.

It is a further object of the present invention to provide a diagnostic kit comprising primers or oligonucleotides specific for PBR RNA suitable for hybridization to PBR RNA and/or amplification of PBR sequences and ancillary reagents suitable for use in detecting PBR RNA in mammalian tissue.

It is another object of the invention to provide a composition effective for inhibiting the binding of PBR ligands, for the purpose of reducing the function of PBR in cells.

It is yet an object of the invention to provide a method for reducing human breast cancer cell proliferation, the method comprising administering to a cell a compound which reduces or inhibits PBR function or expression such that cell proliferation is reduced.

It is yet another object of the present invention to provide a composition effective for reducing or inhibiting peripheral-type benzodiazepine receptor expression or function in metastatic breast tumor cells for use as a treatment for metastatic breast cancer.

It is further another object of the present invention to provide a therapeutic method for the treatment or amelioration of symptoms of metastatic breast cancer, said method comprising providing to an individual in need of such treatment an effective amount of anti-PBR composition in a pharmaceutically acceptable excipient such that PBR expression or function is reduced in said breast cancer cells, or entry of PBR into the nucleus of said breast cancer cells is reduced.

It is yet a further object of the present invention to provide a cDNA sequence encoding PBR found in invasive cells and vectors incorporating all or a fragment of said sequence, and cells, prokaryotic and eukaryotic, transformed or transfected with said vectors, for use in screening agents and drugs which inhibit expression of PBR in such cells.

It is another object of the present invention to provide cells, such as R12, wherein the PBR gene has been interrupted for use in screening agents and drugs which alter PBR expression.

BRIEF DESCRIPTION OF THE DRAWINGS

These and other features, aspects, and advantages of the present invention will become better understood with reference to the following description and appended claims, and accompanying drawings where:

(a) localization of PBR in the epithelium of human breast ducts (horseradish peroxidase staining)[Garnier, M. et al. (1994) *J. Biol. Chem*. 269: 22105-22112].

(b) The hematoxylin counterstaining was omitted in order to examine whether the nucleus of the cells contained immunoreactive PBR protein.

(c) Localization of immunoreactive PBR protein using an FITC-coupled secondary antibody.

(d) Phase contrast microscopy of the same tissue area.

(e) Detection of PBR ligand binding protein using the fluorescent PBR derivative compound 4 [Kozikowski, A. P. et al. (1997) supra]. A filter was used to enhance the detection of low fluorescence levels.

(f) Displacement of the fluorescence with 1000 fold excess of the competitive ligand PK11195 [Kozikowski, A. P. et al. (1997) supra].

FIG. 10 shows PBR expression in aggressive metastatic human breast carcinoma tissue. All biopsies were obtained from the Lombardi Cancer Center at Georgetown University Medical Center. Biopsies were histologically characterized by the pathologist. Paraffin embedded sections of normal breast tissue were immunostained with an anti-PBR antiserum at 1:500 dilution and counterstained with hematoxylin as previously described [Oke, B. O. et al. (1992) supra; Garnier, M. et al. (1993) supra].

(a) Localization of PBR in the epithelium of aggressive metastatic human breast carcinoma (horseradish peroxidase staining) [Garnier, M. et al. (1994), supra].

(b) Hematoxylin counterstaining was omitted in order to examine whether the nucleus of the cells contained immunoreactive PBR protein.

(c) Localization of immunoreactive PBR protein using an FITC-coupled secondary antibody.

(d) Phase contrast microscopy of the same tissue area.

(e) Detection of PBR ligand binding protein using the fluorescent PBR derivative compound 4 [Kozikowski, A. P. et al. (1997) supra].

(f) Displacement of the fluorescence with 1000 fold excess of the competitive ligand PK11195 [Kozikowski, A. P. et al. (1997) supra].

Figure 11:
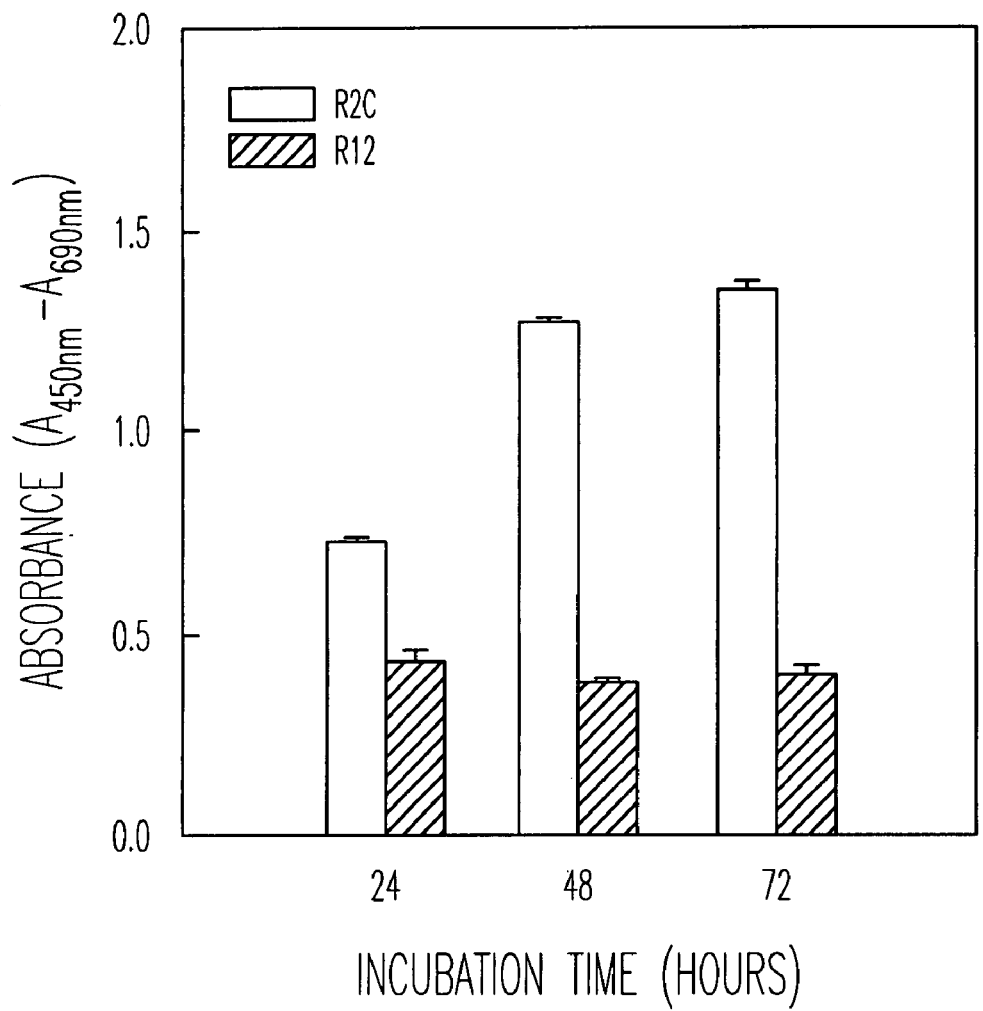

FIG. 11 shows cell proliferation rates of wild-type and mutant R2C tumor cells. Cell proliferation rates of wild type R2C tumor cells and PBR mutant R12 cells. The rate of cell proliferation was determined using the MTT proliferation assay (Boehringer Mannheim). Results shown represent the mean±S.E. of two independent experiments carried out in triplicate.

DETAILED DESCRIPTION

In one embodiment, the present invention provides compositions and methods for detecting peripheral-benzodiazepine receptors (PBR) for the determination of the metastatic potential of a tumor. As discussed above, increased PBR expression correlates with increased aggressive behavior of tumor cells. Invasive tumors invade and grow locally but they do not metastasize. However, the aggressive tumors have the ability to invade and metastasize through the blood vessels to different places of the human body. Tumor metastasis into vital organs (such as lungs) is the most common cause of death.

The correlation between high levels of expression of PBR and metastatic potential is shown in this application for human breast cancer. However, due to the involvement of PBR in cell proliferation, and the expression of PBR in all cells, it is likely that this correlation would exist for other solid tumors and cancers such as prostate cancer, colon cancer, brain tumors, and tumors in steroid producing tissues such as gonadal tumors, to name a few.

The level of expression of PBR, for the purposes of diagnosis or prognosis of a cancer or tumor, can be detected at several levels. Using standard methodology well known in the art, assays for the detection and quantitation of PBR RNA can be designed, and include northern hybridization assays, in situ hybridization assays, and PCR assays, among others. Please see e.g., Maniatis, Fitsch and Sambrook, *Molecular Cloning; A Laboratory Manual* (1982) or *DNA Cloning*, Volumes I and II (D. N. Glover ed. 1985), or *Current Protocols in Molecular Biology*, Ausubel, F. M. et al. (Eds), Wiley & Sons, Inc. for general description of methods for nucleic acid hybridization. Polynucleotides probes for the detection of PBR RNA can be designed from the sequence available at accession number L21950 for the human PBR sequence [Riond, J. et al. (1991) *Eur. J. Biochem.* 195:305-311; Chang, Y. J. et al. (1992) *DNA and Cell Biol.* 11:471-480]. The sequence of PBR from other sources such as bovine [Parola, A. L. et al. (1991) *J. Biol. Chem* 266: 14082-14087] and mouse [Garnier, M. et al. (1994) *Mol. Pharm.* 45:201-211] are also known. In addition, in this application is disclosed a partial DNA sequence of the PBR gene found in invasive cells. Partial cDNA sequences were obtained for both MDA-231 PBR identified as SEQ ID NO:1, and MCF-7 PBR identified as SEQ ID NO:2. The nucleotide sequences obtained revealed four mutations at the DNA level for the gene from MCF-7 and MDA-231, namely, an N to adenine change at nucleotide 83, a guanine to adenine change at nucleotide 362, an adenine to guanine change at nucleotide 408 and a thymine to guanine change at nucleotide 573. An additional change at nucleotide 10 of PBR from MDA-231 was found which was a substitution of guanine for adenine. The changes in the PBR gene encoded by the cDNA of MCF-7 and MDA-231 result in two changes at the amino acid level, a replacement of histidine 162 with arginine and replacement of alanine 147 with a threonine. The amino acids encoded by SEQ ID NO:1 and SEQ ID NO:2 are specified in SEQ ID NO:3. The region surrounding the translation site, and 5' to the translation site has not yet been obtained but may provide key evidence for the differential localization (cytoplasmic versus nuclear) of PBR between the two cell lines. In particular, the PBR sequence derived from MCF-7 or MDA-231 can be used to construct vectors, and produce cell lines which express the altered PBR. Since tumorigenesis is considered to be a multi-step process, it is possible that the changes between the normal PBR and PBR from MCF-7 and MDA-231 represent the initial steps in this process. With this in mind, these cell lines expressing the aberrant PBR can be used to identify what agents would result in a second step towards tumorigenesis, and what drugs would reduce of alter PBR expression. Vector design is known in the art. Transformed cells would include prokaryotic and eukaryotic cells, such as bacteria, most of which do not express PBR, and yeast and mammalian cells. Methods for transforming bacteria and transfecting cells are known in the art. In addition, the sequence of SEQ ID NO:1 or SEQ ID NO:2 can be used to clone the remainder of the PBR sequence of MCF-7 and MDA-231 around the translation start site.

The complete sequence of the PBR, normal or mutant, can be used for a probe to detect RNA expression. Alternatively, a portion or portions of the sequence can be used. Methods for designing probes are known in the art. Polynucleotide sequences are preferably homologous to or complementary to a region of the PBR gene, preferably, the sequence of the region from which the polynucleotide is derived is homologous to or complementary to a sequence which is unique to the PBR gene. Whether or not a sequence is unique to the PBR gene can be determined by techniques known to those of skill in the art. For example, the sequence can be compared to sequences in databanks, e.g., GenBank. Regions from which typical DNA sequences may be derived include but are not limited to, for example, regions encoding specific epitopes, as well as non-transcribed and/or non-translated regions.

For example, RNA isolated from samples can be coated onto a surface such as a nitrocellulose membrane and prepared for northern hybridization. In the case of in situ hybridization of biopsy samples for example, the tissue sample can be prepared for hybridization by standard methods known in the art and hybridized with polynucleotide sequences which specifically recognize PBR RNA. The presence of a hybrid formed between the sample RNA and the polynucleotide can be detected by any method known in the art such as radiochemistry, or immunochemistry, to name a few.

One of skill in the art may find it desirable to prepare probes that are fairly long and/or encompass regions of the amino acid sequence which would have a high degree of redundancy in the corresponding nucleic acid sequences. In other cases, it may be desirable to use two sets of probes simultaneously, each to a different region of the gene. While the exact length of any probe employed is not critical, typical probe sequences are no greater than 500 nucleotides, even more typically they are no greater than 250 nucleotides; they may be no greater than 100 nucleotides, and also may be no greater than 75 nucleotides in length. Longer probe sequences may be necessary to encompass unique polynucleotide regions with differences sufficient to allow related target sequences to be distinguished. For this reason, probes are preferably from about 10 to about 100 nucleotides in length and more preferably from about 20 to about 50 nucleotides.

The DNA sequence of PBR can be used to design primers for use in the detection of PBR using the polymerase chain reaction (PCR) or reverse transciption PCR (RT-PCR). The primers can specifically bind to the PBR cDNA produced by reverse transcription of PBR RNA, for the purpose of detecting the presence, absence, or quantifying the amount of PBR by comparison to a standard. The primers can be any length ranging from 7-40 nucleotides, preferably 10-15 nucleotides, most preferably 18-25 nucleotides homologous or complementary to a region of the PBR sequence. Reagents and controls necessary for PCR or RT-PCR reactions are well known in the art. The amplified products can then be analyzed for the presence or absence of PBR sequences, for example by gel fractionation, by radiochemistry, and immunochemical techniques. This method is advantageous since it requires a small number of cells. Once PBR is detected, a determination whether the cell is an aggressive tumor phenotype can be made by comparison to the results obtained from a normal cell using the same method. The level of aggressiveness can be determined by comparing PBR expression in sample cells to PBR expression of cells with varying levels of aggressive phenotypes since the level of PBR expression correlates with the level of aggressive phenotype of a cell. Increased PBR RNA levels correlate with increased aggressive behavior in a cell.

In another embodiment, the present invention relates to a diagnostic kit for the detection of PBR RNA in cells, said kit comprising a package unit having one or more containers of PBR oligonucleotide primers for detection of PBR by PCR or RT-PCR or PBR polynucleotides for the detection of PBR RNA in cells by in situ hybridization or northern analysis, and in some kits including containers of various reagents used for the method desired. The kit may also contain one or more of the following items: polymerization enzymes, buffers, instructions, controls, detection labels. Kits may include containers of reagents mixed together in suitable proportions for performing the methods in accordance with the invention. Reagent containers preferably contain reagents in unit quantities that obviate measuring steps when performing the subject methods.

In a further embodiment, the present invention provides a method for identifying and quantifying the level of PBR present in a particular biological sample. Any of a variety of methods which are capable of identifying (or quantifying) the level of PBR in a sample can be used for this purpose.

Diagnostic assays to detect PBR may comprise a biopsy or in situ assay of cells from an organ or tissue sections, as well as an aspirate of cells from a tumour or normal tissue. In addition, assays may be conducted upon cellular extracts from organs, tissues, cells, urine, or serum or blood or any other body fluid or extract.

When assaying a biopsy, the assay will comprise, contacting the sample to be assayed with a PBR ligand, natural or synthetic, or an antibody, polyclonal or monoclonal, which recognizes PBR, or antiserum capable of detecting PBR, and detecting the complex formed between PBR present in the sample and the PBR ligand or antibody added.

PBR ligands include the natural ligand diazepan-binding inhibitor (DBI), in addition to natural and synthetic classes of ligands and their derivatives which can be derived from natural sources such as animal or plant extracts. PBR ligands include benzodiazepines such as Ro-4864, diazepam, flunitrazepam, clonazepam, isoquinoline; carboxamides such as PK 11195, PK 14105, PK14067/8 (stereoisomers); imidazopyridines, such as alpidem and zolpidem; 2-aryl-3-idoleacetamides such as FGIN-1-27 and its fluorescent derivative compound 4, and porphyrins such as protophorphyrin IX. In addition to the PBR ligands mentioned above, there is a list of other compounds, essentially those containing aromatic rings, that appear to bind to PBR with different affinities. This list includes dipyridamole, thiazide diuretics, pyrethroid insecticides, carbamazepine, lidocaine, certain steroids, and dihydropyridines. For a review of PBR ligands, please see Papadopoulos, V. (1993) *Endocrine Reviews* 14: 222-240, incorporated in its entirety by reference thereto.

Monoclonal or polyclonal antibodies which recognize PBR can be generated against the complete PBR or against a portion thereof. Persons with ordinary skill in the art using standard methodology can raise monoclonal and polyclonal antibodies to PBR protein (or polypeptide) of the present invention. Polyclonal antibodies are available from the present inventors and commercially available from Sanofi, Inc., France. Materials and methods for producing antibodies are well known in the art (see for example Goding, in, *Monoclonal Antibodies: Principles and Practice*, Chapter 4, 1986). In addition, the protein or polypeptide can be fused to other proteins or polypeptides which increase its antigenicity, thereby producing higher titers of antibodies. Examples of such proteins or polypeptides include any adjuvants or carriers, such as aluminum hydroxide. These antibodies can be used in passive antibody therapy wherein antibodies can be employed to modulate PBR dependent processes such as cell proliferation, and cholesterol transport.

PBR ligands or anti-PBR antibodies, or fragments of ligand and antibodies capable of detecting PBR may be labeled using any of a variety of labels and methods of labeling for use in diagnosis and prognosis of disease, such as breast cancer, particularly for assays such as Positron Emission Tomography and magnetic resonance imaging [Leong, D. et al. (1996) *Alcohol Clin. Exp. Res.* 20:601-605]. Examples of types of labels which can be used in the present invention include, but are not limited to, enzyme labels, radioisotopic labels, non-radioactive isotopic labels, and chemiluminescent labels.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels include $^3$H, $^{111}$In, $^{125}$I, $^{32}$P, $^{35}$S, $^{14}$C, $^{57}$To, $^{58}$Co, $^{59}$Fe, $^{75}$Se, $^{152}$Eu, $^{90}$Y, $^{67}$Cu, $^{21}$Ci, $^{211}$At, $^{212}$Pb, $^{47}$Sc, $^{109}$Pd, $^{11}$C, $^{19}$F, $^{123}$I, etc.

Examples of suitable non-radioactive isotopic labels include $^{157}$Gd, $^{55}$Mn, $^{162}$Dy, $^{52}$Tr, $^{46}$Fe, etc.

Examples of suitable fluorescent labels include a $^{152}$Eu label, a fluorescein label, an isothiocyanate label, a rhodamine label, a phycoerythrin label, a phycodyanin label, an allophycocyanin label, a fluorescamine label, etc.

Examples of chemiluminescent labels include a luminal label, an isoluminal label, an aromatic acridinium ester label, an imidazole label, an acridinium salt label, an oxalate ester label, a luciferin label, a luciferase label, etc.

Those of ordinary skill in the art will know of other suitable labels which may be employed in accordance with the present invention. The binding of these labels to ligands and to antibodies or fragments thereof can be accomplished using standard techniques commonly known to those of ordinary skill in the art. Typical techniques are described by Kennedy, J. H., et al., 1976 (*Clin. Chim. Acta* 70:1-31), and Schurs, A. H. W. M., et al. 1977 (*Clin. Chim Acta* 81:1-40).

Coupling techniques mentioned in the latter are the glutaraldehyde method, the periodate method, the dimaleimide method, and others, all of which are incorporated by reference herein.

The detection of the antibodies (or fragments of antibodies) of the present invention can be improved through the use of carriers. Well-known carriers include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to PBR. Thus, the support configuration may be spherical, as in a bead, or cylindrical, as in the inside surface of a test tube, or the external surface of a rod. Alternatively, the surface may be flat such as a sheet, test strip, etc. Those skilled in the art will note many other suitable carriers for binding monoclonal antibody, or will be able to ascertain the same by use of routine experimentation.

The ligands or antibodies, or fragments of antibodies or ligands of PBR discussed above may be used to quantitatively or qualitatively detect the presence of PBR. Such detection may be accomplished using any of a variety of immunoassays known to persons of ordinary skill in the art such as radioimmunoassays, immunometic assays, etc. Using standard methodology well known in the art, a diagnostic assay can be constucted by coating on a surface (i.e. a solid support) for example, a microtitration plate or a membrane (e.g. nitrocelluolose membrane), antibodies specific for PBR or a portion of PBR, and contacting it with a sample from a person suspected of having a PBR related disease. The presence of a resulting complex formed between PBR in the sample and antibodies specific therefor can be detected by any of the known detection methods common in the art such as fluorescent antibody spectroscopy or colorimetry. A good description of a radioimmune assay may be found in *Laboratory Techniques and Biochemistry in Molecular Biolocgy*. by Work, T. S., et al. North Holland Publishing Company, N.Y. (1978), incorporated by reference herein. Sandwich assays are described by Wide at pages 199-206 of *Radioimmune Assay Method*, edited by Kirkham and Hunter, E. & S. Livingstone, Edinburgh, 1970.

The determination of elevated levels of PBR is done relative to a sample with no detectable tumor. This may be from the same patient or a different patient. For example, a first sample may be collected immediately following surgical removal of a solid tumor. Subsequent samples may be taken to monitor recurrence of tumor growth and/or tumor cell proliferation. Additionally, other standards may include cells of varying aggressive phenotype such that an increase or decrease in aggressive phenotype can be assessed.

The distinct subcellular localization of PBR in the cytoplasm of epithelial cells of normal breast ducts and the absence of staining in the nucleus, in contrast with the localization of PBR in aggressive carcinomas in the nucleus and the perinuclear area of the aggressive tumor cells provides a simple method for diagnosing the aggressive phenotype of a tumor cell. Immunostaining using labeled PBR ligand or labeled PBR antibody or fragment of ligand or antibody capable of binding to PBR and determining the subcellular location of PBR in the cellular samples provides yet another diagnostic assay of the present invention. In addition, antiserum which recognizes PBR can also be used along with a secondary antibody reactive with the primary antibody. Immunostaining assays are well known in the art, and are additionally described in the Examples below with respect to breast cancer cells and biopsies.

The diagnostic methods of this invention are predictive of proliferation and metastatic potential in patients suffering from breast cancinomas including lobular and duct carcinomas, and other solid tumors, carcinomas, sarcomas, and cancers including carcinomas of the lung like small cell carcinoma, large cell carcinoma, squamous carcinoma, and adenocarcinoma, stomach carcinoma, prostatic adenocarcinoma, ovarian carcinoma such as serous cystadenocarcinoma and mucinous cytadenocarcinoma, ovarian germ cell tumors, testicular carcinomas, and germ cell tumors, pancreatic adenocarcinoma, biliary adenocarcinoma, heptacellular carcinoma, renal cell adenocarcinoma, endometrial carcinoma including adenocarcinomas and mixed Mullerian tumors (carcinosarcomas), carcinomas of the endocervix, ectocervix, and vagina such as adenocarcinoma and squamous carcinoma, basal cell carcinoma, melanoma, and skin appendage tumors, esophageal carcinoma, carcinomas of the nasopharyns and oropharynx including squamous carcinoma and adenocarcinomas, salivary gland carcinomas, brain and central nervous system tumors including tumors of glial, neuronal, and meningeal origin, tumors of peripheral nerve, soft tissue sarcomas and sarcoms of bone and cartilage. Cells of these tumors which express increased levels of PBR RNA or PBR protein, and/or PBR which localizes to the nucleus are considered acquiring the aggressive tumor phenotype and can result in increased metastasis.

Agents which decrease the level of PBR (i.e. in a human or an animal) or reduce or inhibit PBR activity may be used in the therapy of any disease associated with the elevated levels of PBR such as metastatic cancer, for example breast cancer, or diseases associated with increased cell proliferation or increased cholesterol transport into the cell. An increase in the level of PBR is determined when the level of PBR in a tumor cell is about 2-3 times the level of PBR in the normal cell, up to about 10-100 times the amount of PBR in a normal cell. Agents which decrease PBR RNA include, but are not limited to, one or more ribozymes capable of digesting PBR RNA, or antisense oligonucleotides capable of hybridizing to PBR RNA such that the translation of PBR is inhibited or reduced resulting in a decrease in the level of PBR. These antisense oligonucleotides can be administered as DNA, as DNA entrapped in proteoliposomes containing viral envelope receptor proteins [Kanoda, Y. et al. (1989) *Science* 243:375] or as part of a vector which can be expressed in the target cell such that the antisence DNA or RNA is made. Vectors which are expressed in particular cell types are known in the art, for example, for the mammary gland, please see Furth, (1997) (*J. Mammary Gland Biol. Neopl*. 2:373) for examples of conditional control of gene expression in the mammary gland. Alternatively, the DNA can be injected along with a carrier. A carrier can be a protein such as a cytokine, for example interleukin 2, or polylysine-glycoprotein carrier. Such carrier proteins and vectors and methods of using same are known in the art. In addition, the DNA could be coated onto tiny gold beads and said beads introduced into the skin with, for example, a gene gun [Ulmer, J. B. et al. (1993) *Science* 259:1745].

Alternatively, antibodies, or compounds capable of reducing or inhibiting PBR, that is reducing or inhibiting either the expression, production or activity of PBR, such as antagonists, can be provided as an isolated and substantially purified protein, or as part of an expression vector capable of being expressed in the target cell such that the PBR-reducing or inhibiting agent is produced. In addition, co-factors such as various ions, i.e. Ca2+[Calvo, D. J. and Medina, J. H. (1993) *J. Recept. Res*. 13:975-987], or anions, such as halides or anion channel blockers such as DIDS (4,4'diisothiocyanostilbene-2,2'-disulfonic acid), an ion transport blocker [Skolnick, P. (1987) *Eur. J. Pharmacol*. 133:205-214], or factors which affect the stability of the receptor such as lipids, for example, the phospholipids phosphatidylserine and phosphatidylinositol whereby the presence of the phospholipids is required for receptor activity [Moynagh, P. N. and Williams, D. C. (1992) *Biochem. Pharmacol.* 43:1939-1945] can be administered to modulate the expression and function of the receptor. These formulations can be administered by standard routes. In general, the combinations may be administered by the topical, transdermal, intraperitoneal, oral, rectal, or parenteral (e.g. intravenous, subcutaneous, or intramuscular) route. In addition, PBR-inhibiting compounds may be incorporated into biodegradable polymers being implanted in the vicinity of where drug delivery is desired, for example, at the site of a tumor or implanted so that the PBR-inhibiting compound is slowly released systemically. The biodegradable polymers and their use are described, for example, in detail in Brem et al.(1991) *J. Neurosurg.* 74:441-446.

These compounds are intended to be provided to recipient subjects in an amount sufficient to effect the inhibition of PBR. Similarly, agents which are capable of negatively affecting the expression, production, stability or function of PBR, are intended to be provided to recipient subjects in an amount sufficient to effect the inhibition of PBR. An amount is said to be sufficient to "effect" the inhibition or induction of PBR if the dosage, route of administration, etc. of the agent are sufficient to influence such a response.

In line with the function of PBR in cell proliferation, agents which stimulate the level of PBR, such as agonists of PBR, may be used in the therapy of any disease associated with a decrease of PBR, or a decrease in cell proliferation, wherein PBR is capable of increasing such proliferation, e.g. developmental retardation. PBR has also been shown to be involved in cholesterol transport, therefore, an agent or drug which results in an increase in expression, function, or stability of PBR can be used to increase cholesterol transport into cells. Diseases where cholesterol transport is deficient include lipoidal adrenal hyperplasia, and diseases where there is a requirement for increased production of compounds requiring cholesterol such as myelin and myelination including Alzheimer's disease, spinal chord injury, and brain development neuropathy [Snipes, G. and Suter, U. (1997) Cholesterol and Myelin. In: *Subcellular Biochemistry*, Robert Bittman (ed.), vol. 28, pp. 173-204, Plenum Press, New York], to name a few.

In providing a patient with antibodies, or fragments thereof, capable of binding to PBR, or an agent capable of inhibiting PBR expression or function to a recipient patient, the dosage of administered agent will vary depending upon such factors as the patient's age, weight, height, sex, general medical condition, previous medical history, etc. Similarly, when providing a patient with an agent or agonist capable of inducing or increasing expression or function of PBR, the dosage will vary depending upon such factors as the patient's age, weight, height, medical history, etc. In general, it is desirable to provide the recipient with a dosage of agent which is in the range of from about 1 pg/kg to 10 mg/kg (body weight of patient), although a lower or higher dosage may be administered.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The compounds of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in *Remington's Pharmaceutical Sciences* [16th ed., Osol, A. ed., Mack Easton Pa. (1980)]. In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly (methylmethacrylate)microcapsules, respectively, or in colloidal drug delivery systems, for example, liposomes, albumin microspheres, microemulsions, nanoparticles, and nanocapsules or in macroemulsions. Such techniques are disclosed in *Remington's Pharmaceutical Sciences* (1980).

Having now generally described the invention, the same will be more readily understood through reference to the following examples which are provided by way of illustration, and are not intended to be limiting to the present invention, unless specified.

The following MATERIALS AND METHODS were used in the examples that follow.

Cell Culture—Human breast cancer cell lines (BT549, HS-578-T, MCF-7, MDA-231, MDA-435, MDA-468, T47D, and ZR-75-1) were obtained from the Lombardi Cancer Center, Georgetown University Medical Center. The U937 human histiocytic lymphoma cell line was obtained from the American Type Culture Collection (Rockville, Md.). MA-10 mouse Leydig tumor cells were a gift from Dr. Mario Ascoli (University of Iowa) and were maintained in Waymouth's MB752/1 medium supplemented with 15% horse serum as previously described [Papadopoulos et al., (1990) *J. Biol. Chem* 265:3772-3778]. All cell lines were cultured on polystyrene culture dishes (Corning) and, with the exception of the U937 cell line, grown in Dulbecco's modified Eagle medium (DMEM) supplemented with 10% fetal bovine serum (FBS). The U937 cell line were grown in RPMI medium (Gibco) supplemented with 10% FBS.

Radioligand Binding Assays—Cells were scraped from 150 mm culture dishes into 5 ml phosphate buffered saline (PBS), dispersed by trituration, and centrifuged at 500×g for 15 min. Cell pellets were resuspended in PBS and assayed for protein concentration. [$^3$H]PK11195 binding studies on 50?g of protein from cell suspensions were performed as previously described [Papadopoulos et al 1990, supra; Garnier et al., (1994) *Molecular Pharmacology* 45:201-211]. Scatchard plots were analyzed by the LIGAND program [Munson, (1980) *Anal. Biochem.* 107:220]. Specific binding of [$^3$H]PK11195 (2.0 nM) to MDA-231 cells was measured in the presence or absence of the indicated concentrations of competing PBR ligands as previously described (Garnier, 1994, supra). IC50 estimation was performed using the LIGAND program (Munson, 1980, supra).

Protein Measurement—Protein levels were measured by the Bradford method [Bradford (1976) *Anal. Biochem.* 72:248-2554] using the Bio-Rad Protein Assay kit (Bio-Rad Laboratories) with bovine serum albumin as a standard.

Transmission Electron Microscopy—MDA-231, MCF-7ADR, and MCF-7 cells cultured on 25 cm² culture dishes (Corning) were first washed with PBS for 5 min three times. The cells were then fixed with a solution of 1% paraformaldehyde, 2% gluteraldehyde, and 0.1M PBS for 15 min at room temperature and then washed three times with PBS. The cells were then embedded in Epon-araldite and further processed as previously described [Li et al. (1997) *Endocrinology* 138:1289-1298].

Northern Analysis—The levels of hPBR mRNA from MDA-231, MCF-7, ADR, and U937 cells were compared by Northern Blot analysis. Total cellular RNA was isolated from cells grown on 150 mm culture dishes by the addition of 4.5 ml RNAzol B (TEL-TEST, Inc.) and 0.45 ml chloroform. After vigorous shaking and centrifugation at 9,000×g for 30 min, the aqueous phase was transferred to a fresh tube and mixed 1:1 with isopropanol (v:v), stored at −20° C. for 2 hr, and centrifuged at 9,000×g for 30 min. The RNA pellet was then washed with 75% ethanol and centrifuged 7,500×g for 8 min. The pellet was then air dried and resuspended in formazol. RNA concentrations and purity were determined at 260/280 nm.

20 ug of total RNA from each cell line were run on 1% agarose gels containing 1×MOPS and 5.3% formaldehyde using the 0.24 to 9.5 kb RNA Ladder (GIBCO) as a size marker. Gels were then transferred overnight to nylon membranes (S&S Nytran, Schleicher & Schuell, Keene, N.H.) (Maniatis, 1989). A 0.2 kb human PBR (hPBR) cDNA fragment (derived from the pCMV5-PBR plasmid vector containing the full length hPBR kindly given by Dr. Jerome Strauss, University of Pennsylvania, Pa.) was radiolabeled with [?-$^{32}$P]dCTP using a random primers DNA labeling system (Life Technologies, Gaithersburg, Md.). The filter was first prehybridized overnight at 68° C. in 6×SSC, 0.5% SDS, and 100 ug/ml denatured, fragmented, salmon sperm DNA. After hybridization, the membrane was washed twice with 2×SSC, 0.5% SDS for 10 min, once with 0.2×SSC, 0.5% SDS for 30-60 min at room temperature, and once with 0.2×SSC, 0.5% SDS for 30 min at 60° C. Autoradiography was performed by exposing the blots to X-OMAT AR film (Kodak, Rochester, N.Y.) at −70° C. for 4-48 hr. Quantification of PBR mRNA was carried out using the SigmaGel software (Jandel Scientific, San Rafael, Calif.).

Partial cDNA Sequencing—PBR cDNAs were prepared from total MDA-231 and MCF-7 RNA using the Perkin Elmer RT-PCR Kit (Branchburg, N.J.). PCR was performed on cDNAs using primers designed from the known human sequence (Riond, 1991, supra). Labeling of PCR products was performed using the ABI PRISM Dye Terminator Cycle Sequencing Ready Reaction Kit (Perkin Elmer, Branchburg, N.J.). Labeled PCR product was then given to the Lombardi Sequencing Core Facility (Georgetown University Medical Center, Washington, D.C.) for sequence analysis.

Fluorescent Microscopy with the compound 4 fluorescent PBR Ligand—MA-10, MDA-231, MCF-7, and ADR cells were grown on glass coverslips as previously described [Kozikowski et al. (1997) *J. Med. Chem.* 40: 2435-2439]. Cells were then washed twice with sterile PBS and incubated for 45 min with 1 uM compound 4, a fluorescent derivative of the PBR ligand FGIN-27, with or without a competing PBR ligand, FGIN-27, at a concentration of 100 uM. After the incubation period, the cells were washed with PBS and examined by fluorescent microscopy using an Olympus BH-2 fluorescence microscope.

Immunocytochemistry of MDA-231 Cells—MDA-231 cells were cultured overnight on 8-chambered SuperCell Culture Slides (Fisher Scientific, Pittsburgh, Pa.) at a concentration of approximately 50,000 cells/chamber. Cells were then fixed in 70% EtOH for 15 min at 4° C. After washing 3× in distilled $H_2O$ for 2 min each, the fixed cells were incubated overnight at 4° C. with either PBR [Amri et al. (1996) *Endocrinology* 137:5707-5708] or DBI [Garnier et al. (1993) Endocrinology 132: 444-458] polyclonal antisera at concentrations of 1:100, 1:200, 1:500, or 1:1,000. After incubation with primary antiserum, slides were washed 3× in PBS for 2 min each. Slides were then incubated at room temperature for 1 h with horseradish peroxidase-coupled goat anti-rabbit secondary antibody diluted 1:1,000 in PBS supplemented with 10% calf serum. After washing slides 3× in PBS for 2 min each, fresh $H_2O_2$ diluted 1:1,000 with 3-amino-9-ethyl carbazole (AEC) was added and slides were incubated for 1 h at 37° C. Slides were then rinsed in distilled H20 and counterstained with hematoxylin for 2 min, washed with tap $H_2O$ and left in PBS until cells turn blue (approximately 30 s), and rinsed in distilled $H_2O$ before mounting with Crystal/Mount.

Nuclear Uptake of $^3$H-Cholesterol—Nuclei were isolated from MDA-231, MCF-7, and as described by Elango et al (1997). Isolated nuclei were resuspended in 1 ml ice-cold PBS. $^3$H-cholesterol uptake in MDA-231 and MCF-7 nuclei was examined using the indicated concentrations of PK11195 incubated in 0.3 ml final volume in the presence of 6.7 nM [1,2]$^3$H-cholesterol (50.0 Ci/mmol) and 3 ug nuclear protein (determined using the Bradford method as previously described) for 60 min at 37° C. Samples were then centrifuged at 500×g for 30 min and pellets were washed in 500 ml ice-cold PBS. After a second centrifugation at 500×g for 30 min, 200 ul 1.0 N NaOH was then added to the pellets and incubated overnight at 37° C. After incubation, 200 ul 1.0 N HCl was added and samples were vigorously vortexed. 3 ml scintillation cocktail (Eco-Lite) was then added prior to reading radioactivity on a Wallac 1409 Liquid Scintillation Counter.

BrdU Cell Proliferation Assays and BrdU-labeling of MDA-231 Cells—MDA-231 cells were plated on 96-well plates (Corning) at a concentration of approximately 10,000 cells/well (24 h incubation) or approximately 5,000 cells/well (48 h incubation) in DMEM supplemented with 0.1% FBS. The cells were then incubated in either 0.1% or 10% FBS with various concentrations of PK11195 (10-10, 10-9, 10-8, 10-7, 10-6, 10-5, or 10-4 M) for both 24 h or 48 h. Differences in cell proliferation were analyzed by measuring the amount of 5-bromo-2'deoxyuridine (BrdU) incorporation as determined by the BrdU ELISA (Boehringer Mannheim).

EXAMPLE 1

Figure 1:
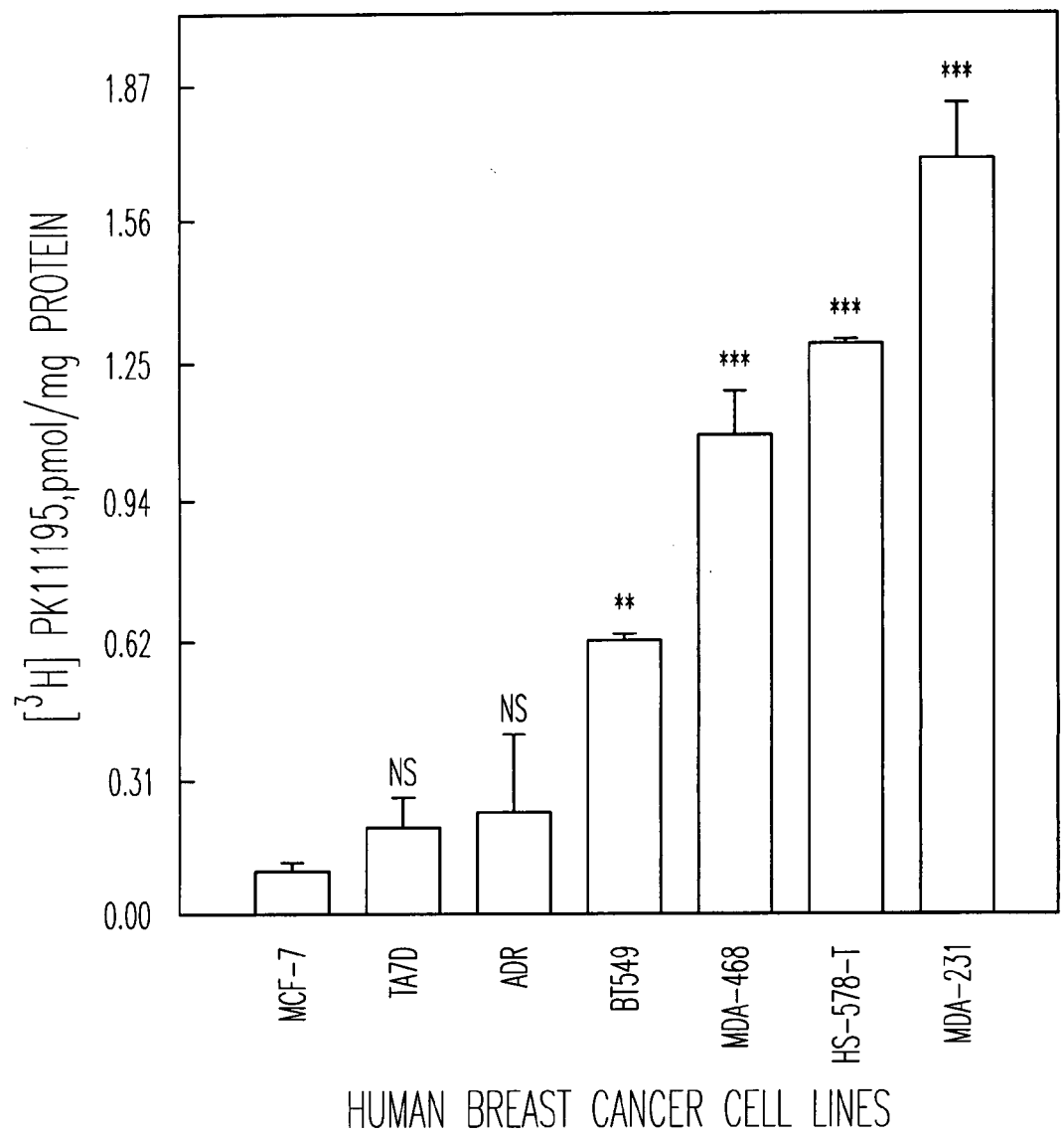
FIG. 1 demonstrates specific PBR binding characteristics of various human breast cancer cell lines. PK11195 specific binding was determined using increasing concentrations of cellular protein (figure shows specific PBR binding at 50 ug of protein) for each of the indicated cell lines described in Table 1. *, $p<0.05$; , $p<0.01$; NS, not significant.

Increased Expression of the Peripheral-Type Benzodiazepine Receptor Corresponds With Increased Aggressive Phenotype in Human Breast Cancer Cell Lines In order to establish a correlation between PBR expression and increased aggressive behavior in cancer we chose to examine this proposed phenomenon in human breast cancer. To this end, binding studies were initially performed on nine human breast cancer cell lines using the PBR-specific high affinity ligand PK11195. The results from these early experiments indicate that those cell lines with a more invasive and chemotactic potential such as HS-578-T and MDA-231 display dramatically increased levels of PBR binding relative to non-aggressive cell lines such as ZR-75-1, T47D, and MCF-7 (Table 1 and FIG. 1).

TABLE 1

Comparison of Invasive Characteristics of
Human Breast Cancer Cell Lines to PBR Expression.

| Cell Line | Estrogen Receptor | Vimentin | Invasion | Chemotaxis | CD44 | PBR |
|---|---|---|---|---|---|---|
| ZR-75-1 | + | − | + | + | − | − |
| T47D | + | − | + | + | − | + |
| MCF-7 | + | − | + + | + + | + | + |
| MDA-435 | − | + | + + + | + + | + + + | + |
| ADR | − | + | + + + | + + | + + | + + |
| BT549 | − | + | + + + + + | + + + + | + + + + | + + + |
| MDA-468 | − | ± | + | + + + | + + + + | + + + + |
| HS578-T | − | ± | + + + + + | + + + + | + + + + + | + + + + + |
| MDA-231 | − | + | + + + + + | + + + + + | + + + | + + + + + |

The various characteristics of the human breast cancer cell lines described above are from Culty et al, 1993, J. Cell Phys. 160: 275–286. The presence or absence of estrogen receptor and vimentin are indicated by either a + or =, respectively. The invasive and chemotaxis assays were determined by quantifying the migration of cells in Boyden chamber assays using fibroblast conditioned medium as the chemo-attactant. Chemoinvation was studied using polycarbonate filters coated with a uniformlayer of matrigel constituting a barrier that the cells had to degrade in order to reach the filters and migrate through them. To determine the chemotactic behavior of the cells, the filters were coated with a thin layer of collagen IV that promotes cell attachment and allows the free migration of the cells toward the gradient of fibroblast conditioned medium. Invasion, chemotactic, and PBR binding were graded as % of MDA-231 values (−, not detectable, +, 0–20%; + +, 20–40%, + + +, 40–60%, + + + +, 60–8%, + + + + +, >80%). The relative amounts of PBR were determined with binding assays in which increasing concentrations of cellular protein were incubated with a constant level of [$^3$H]PK11195 (6 nM). Non-specific binding was determined in the presence of cold PK11195.

Figure 2A:
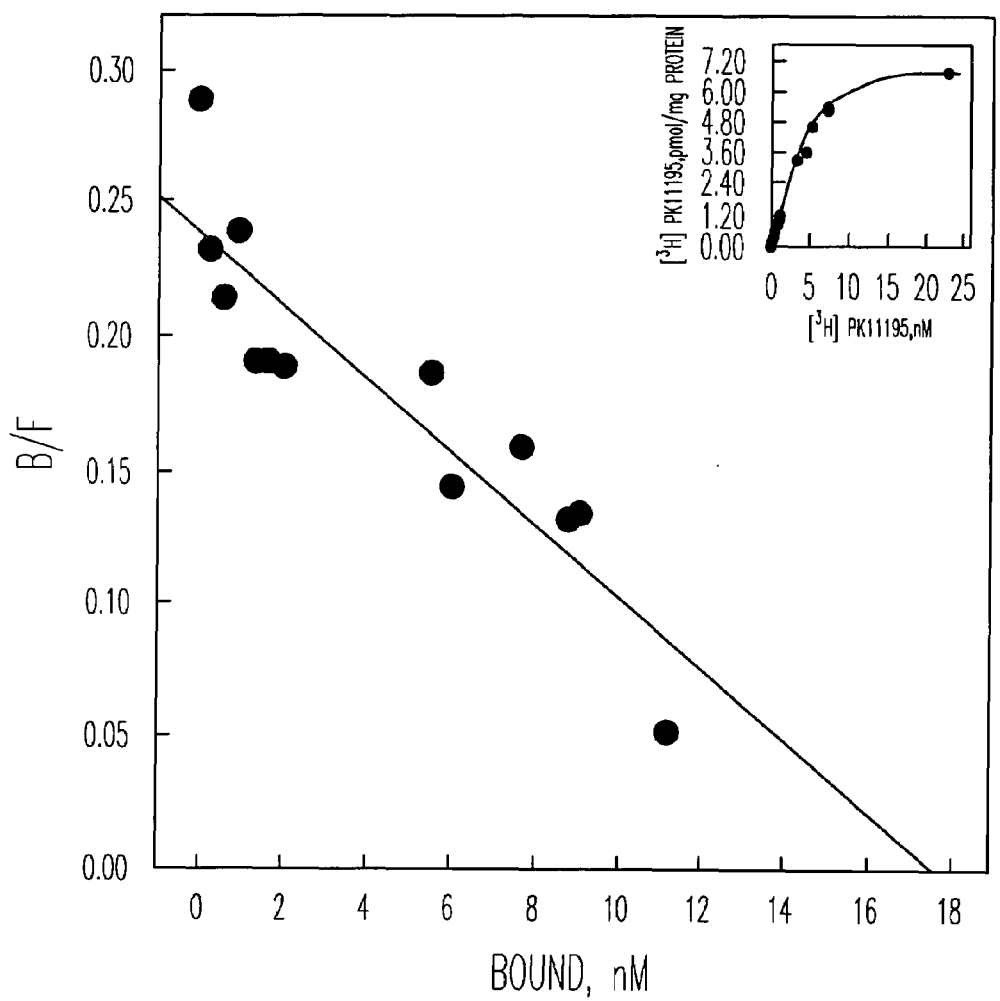
FIG. 2 represents Scatchard plots and saturation isotherms for MDA-231 and ADR human breast cancer cell lines. [$^3$H]PK11195 binding studies were carried out for ADR (A), MDA-231 (B), and MCF-7 cell lines as described [Papadopoulos, V. et al. (1990) *J. Biol. Chem* 265: 3772-3779]. Saturation isotherms and Scatchard plot analyses for MDA-231 (B) and ADR (A) cells are shown. Although specific binding could be detected in MCF-7 cells, an accurate Scatchard plot analysis of the data generated could not be performed.
Figure 2B:
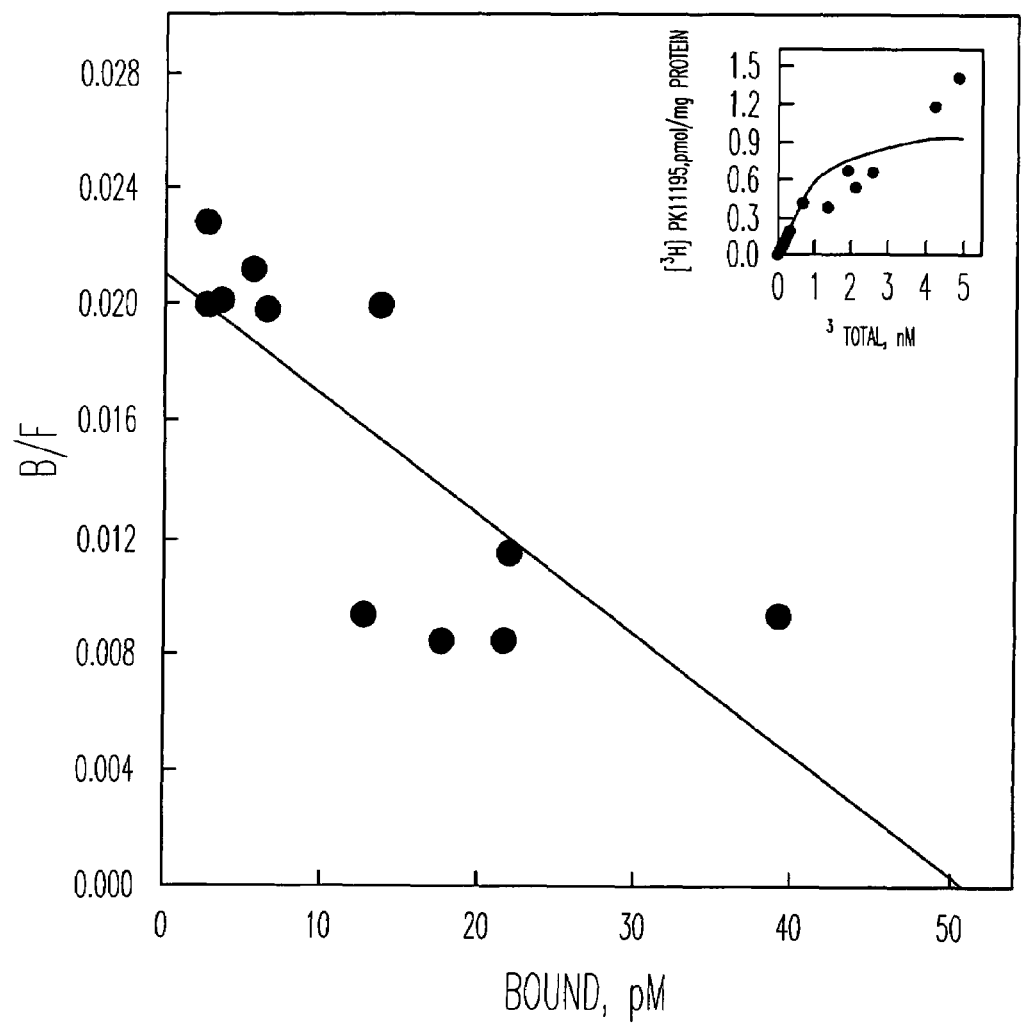
Figure 3:
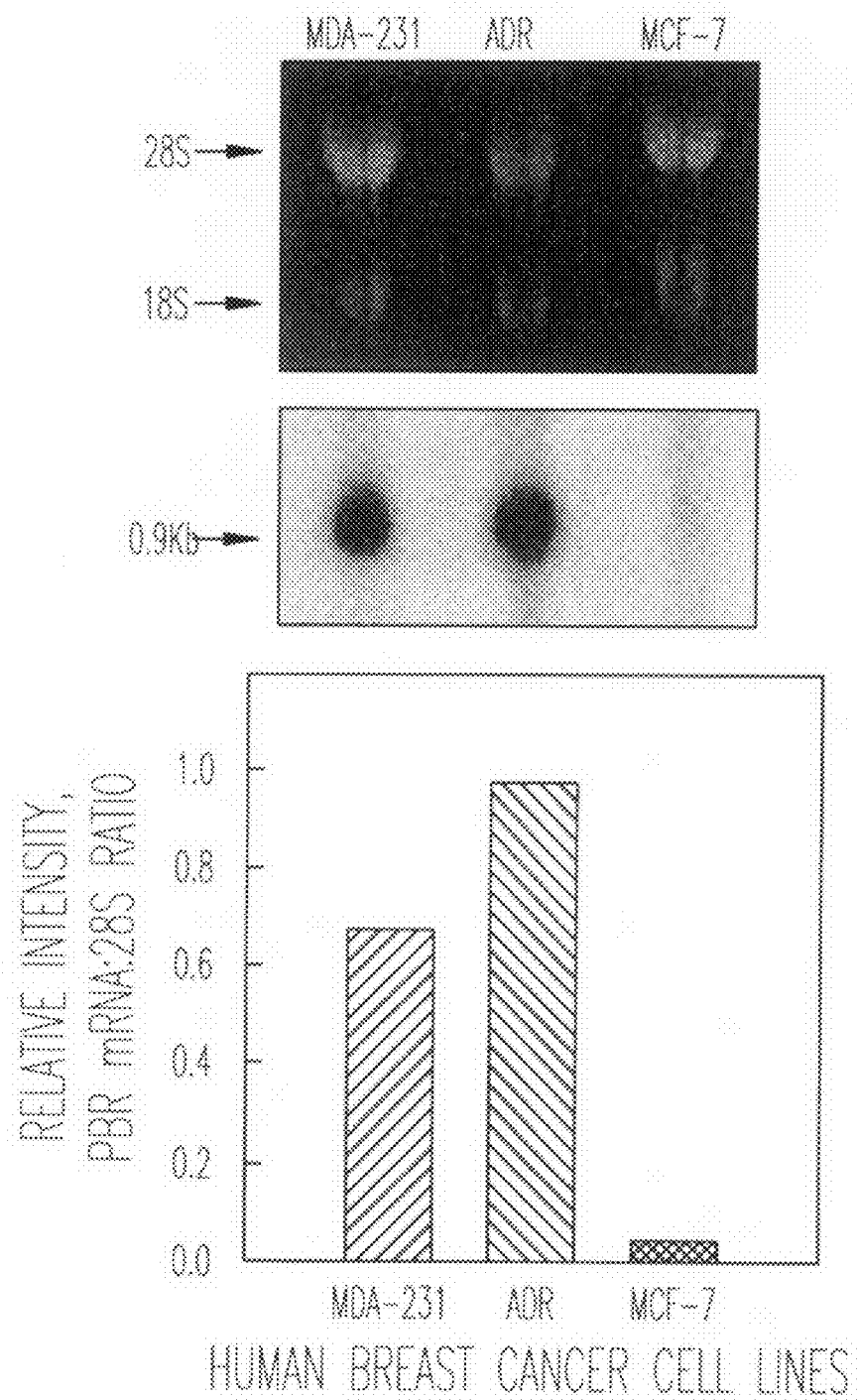
FIG. 3 shows PBR mRNA expression in MDA-231, ADR, and MCF-7 cell lines. Total RNA was isolated from MDA-231, ADR, and MCF-7 cells and loaded onto a 1% formaldehyde gel at a concentration of 10 ug/lane. Northern blots were incubated with $^{32}$P-labeled hPBR probe and exposed to XOMAT Kodak film. Top, 28S and 18S rRNA visualized by ethidium bromide staining. Middle, autoradiogram of the blot. PBR migrates at 0.9 Kb. Bottom, relative intensity of the PBR mRNA/28S ribosomal RNA.

Further, the MCF-7 adriamycin-resistant derivative cell line, MCF-7ADR (ADR), which expresses medium invasive and chemotactic potential as well as intermediate levels of CD44, expressed approximately 20 to 40% PBR binding relative to the MDA-231 cell line (Table 1). Scatchard analysis of PBR binding in the MDA-231 and ADR cell lines further shows each to have a Bmax of 8.7±1.4 and 1.3±0.23 pmol/mg protein, respectively (Table 2 and FIGS. 2a and 2b). Despite obtaining specific PK11195 binding, the low levels of binding were inadequate for estimating the binding characteristics using Scatchard plot analysis (Table 2). RNA (Northern) blot analysis was performed in order to determine if the differences shown in PBR binding between the cell lines reflects differential expression of PBR MRNA. As shown in FIG. 3, MDA-231 cells express approximately 20-fold more PBR mRNA than MCF-7 cells. This result fits with the correlation between PBR expression and increased aggressive behavior between these cell lines. The amount of PBR mRNA expressed in the ADR cell line does not conform to this, however. In fact, ADR cells express almost 1.5-fold more PBR mRNA than MDA-231 cells (FIG. 3). This seemingly anomalous result will be discussed later.

TABLE 2

PBR Binding Characteristics of MDA-231, ADR, and MCF-7 Cells

| | PK11195 | |
|---|---|---|
| Cell Line | $K_D$ (nM) | $B_{max}$ (pmol/mg protein) |
| MDA-231 | 7.8 ± 1.8 | 8.7 ± 1.4 |
| ADR | 1.9 ± 0.47 | 1.3 ± 0.23 |
| MCF-7 | ND | ND |

Ligand binding studies on MDA-231, ADR, and MCF-7 cells (50 μg) were performed using [3H]PK11195 as we described [Papadopoulos et al. (1990) J. Biol. Chem. 265: 3772–3779]. The results were analyzed by Scatchard plot carried out using the LIGAND program (Munson, 1980, supra).

ND, not detectable because Scatchard plot analysis of the binding data could not be performed although low levels of specific binding could be seen, indicating the presence of PBR but at extremely low levels.

Previous studies demonstrated that, in most tissues, PBR is primarily localized to the mitochondria (Papadopoulos, 1993, supra). In order to rule out the possibility that the differences between aggressive and non-aggressive human breast cancer cell lines is not due to differences in mitochondrial content morphometry analysis was performed on transmission electron micrographs on two of the extreme cell lines, MDA-231 and MCF-7 (Data not shown). Numerous morphological differences between the two cell lines, including differences in vacuole content and the presence of mysterious dark bodies, that may reflect their differences in metabolic activity. Morphometric analysis indicates that the larger MCF-7 mitochondria cover the same surface area/cell in the micrographs as do the MDA-231 mitochondria.

Figure 4A:
FIG. 4 shows subcellular localization of PBR using the compound 4 PBR fluorescent probe. MA-10 (a), MCF-7(b), and MDA-231 (c,d) cells were cultured on coverslips and incubated with compound 4 (1 uM) for 45 min at 37° C. MDA-231 cells were incubated with compound 4 (1 uM) for 45 min at 37° C. in the presence of 100 uM of FGIN-27 (e), the non-fluorescent PBR ligand used to develop compound 4 [Kozikowski, A. P. et al. (1997) *J. Med. Chem*. 40: 2435-2439]. At the end of the incubation time, the cells were washed, and PBR was localized by fluorescence microscopy. (f), phase-contrast of the same image as shown in e.
Figure 4B:
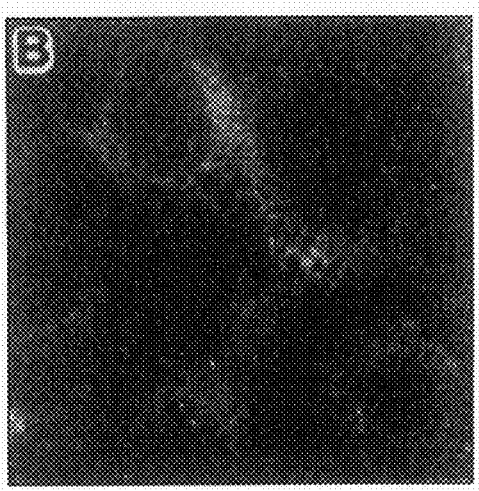
Figure 4C:
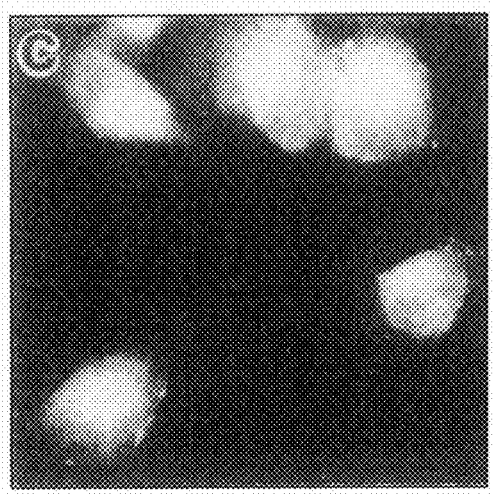
Figure 4D:
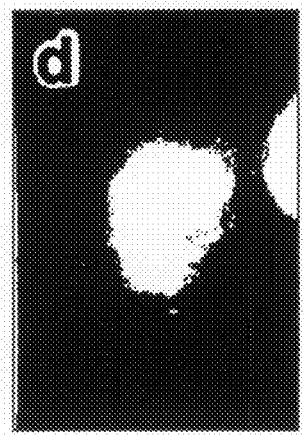
Figure 4E:
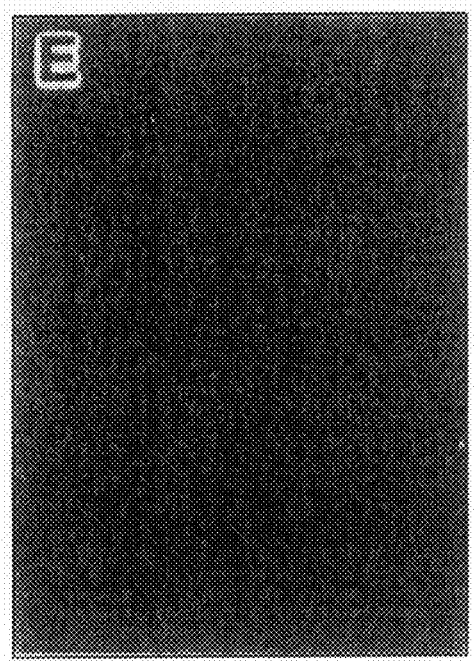
Figure 4F:
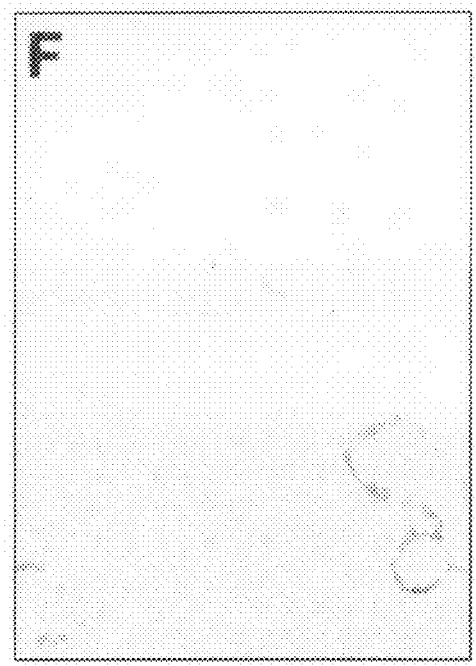
Figure 5:
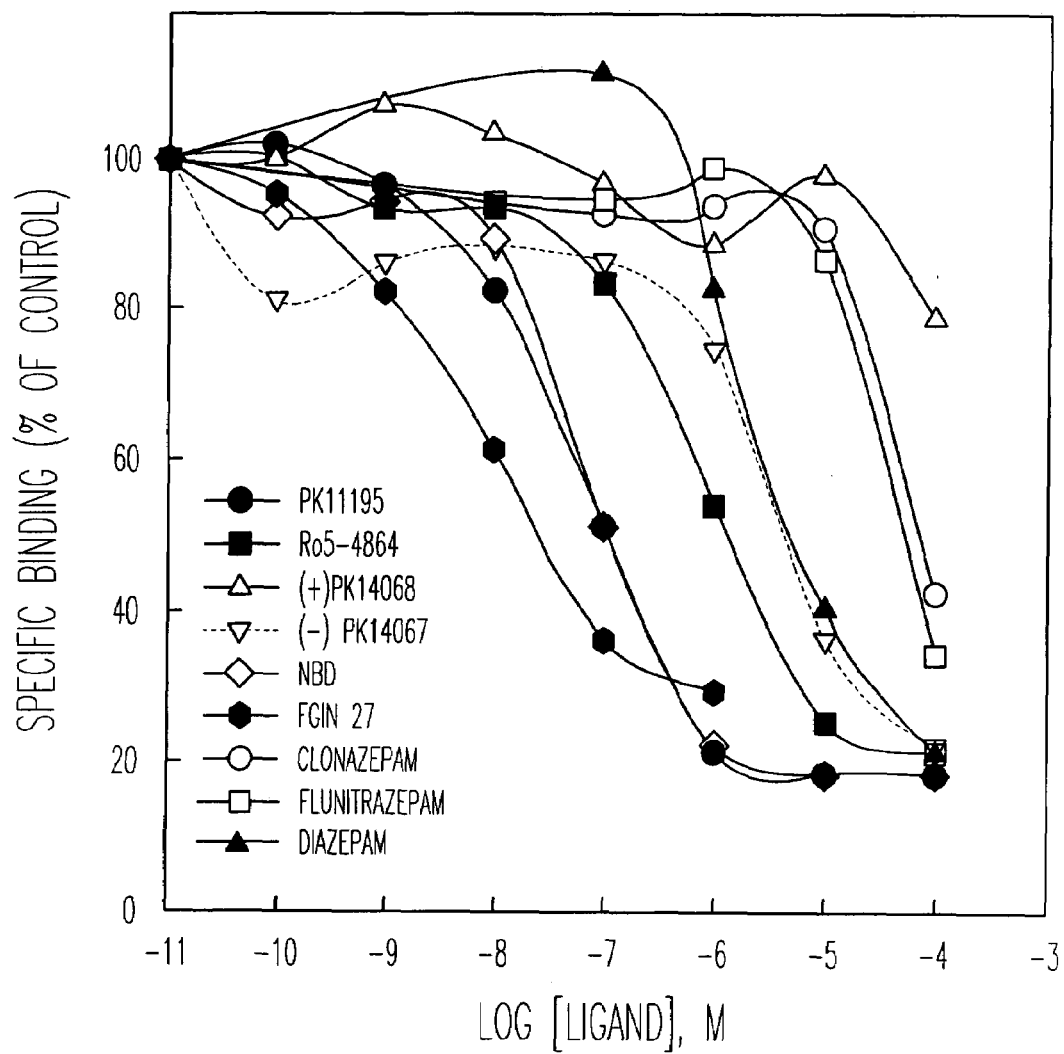
FIG. 5 demonstrates the binding specificity of MDA-231 PBR. Specific binding of [$^3$H]PK11195 (2 nM) to MDA-231 cells was measured in the presence of the indicated concentrations of each competing ligand [Papadopoulos, V. et al. (1990) supra]. 100% binding corresponds to 21 fmol [$^3$H] PK11195. All data are expressed as the means of quadruplicate assays.

In order to further characterize the differences between these human breast cancer cell lines, subcellular localization was carried out using compound 4, the fluorescent derivative of FGIN-27, a specific PBR ligand (Kozikowski et al., 1997, supra). PBR has previously been shown to localize primarily to the outer mitochondrial membrane in MA-10 mouse tumor Leydig cells, the cell line used to characterize the only known PBR function (Papadopoulos, 1993, supra). In MA-10 cells, compound 4 fluorescent labeling is localized to the cytoplasm, presumably to the mitochondria (FIG. 4a). Similar to MA-10 cells, PBR is localized almost exclusively to the cytoplasm in MCF-7 cells (FIG. 4b). Strikingly however, PBR localizes primarily to the nucleus in MDA-231 cells (FIG. 4c,d). This fluorescence indicates localization to either the nucleoplasm (FIG. 4c) or the peri-nuclear envelope (FIG. 5d). The displacement of fluorescent binding by 100 uM FGIN-27 indicates that compound 4 labeling is specific for PBR (FIG. 4e). Scatchard analysis of [$^3$H] PK11195 binding to nuclei isolated from MDA-231 cells revealed a KD of 10.3±8.4 nM and a Bmax of 6.9±4.8 pmol/mg nuclear protein (Table 3). Similar analysis of nuclei isolated from MCF-7 cells yielded a KD of 7.6±4.6 nM and a Bmax of 0.4±0.2 pmol/mg nuclear protein (Table 3). While not shown, in ADR cells, PBR localizes chiefly to the cytoplasm, although nuclear fluorescence is also seen. Further, anti-PBR immunostaining of MDA-231 cells supports the nuclear localization of the receptor seen with the fluorescent compound 4 (data not shown).

TABLE 3

PBR-binding Characteristics of MDA-231 and MCF-7 Nuclei

| Cell Line | PK11195 | |
|---|---|---|
| | $K_D$ (nM) | $B_{max}$ (pmol/mg protein) |
| MDA-231 | 10.3 ± 8.4 | 6.9 ± 4,8 |
| MCF-7 | 7.6 ± 4.6 | 0.4 ± 0.2 |

Intact nuclei were isolated from MDA-231 and MCF-7 cells. Ligand binding studies were performed and analysed as described in Table 2.

EXAMPLE 2

PBR Found in the MDA-231 Human Breast Cancer Cell Line is Similar to PBR Found in Other Human Tissues Given the numerous differences between both the expression and localization of PBR in MDA-231 cells and the other human breast cancer cell lines studied, as well as previous published reports, it became important to determine if we were dealing with the same receptor. The first step towards this end was to establish a pharmacological profile for MDA-231 PBR. Displacement of [$^3$H] PK11195 by increasing concentrations of various PBR ligands is similar to the pharmacological profile previously reported for human PBR (FIG. 5) (Chang et al. (1992), supra). Next we obtained partial PBR cDNA sequences for both MDA-231 and MCF-7 PBR. The nucleotide sequences obtained revealed several point mutations resulting in two amino acid replacements replacing alanine 147 with a threonine and a replacing of histidine 162 with arginine in both MDA-231 and MCF-7. Given that this mutation occurs in both cell lines it is unsure what role it plays in cancer pathogenesis. Despite many efforts, a sequence could not be obtained for the region immediately surrounding the translation start sight. The region 5' to the start sight may provide key evidence for the differential localization (cytoplasmic versus nuclear) of PBR between these two cell lines.

EXAMPLE 3

A Functional Role for PBR in Human Breast Cancer

Figure 6:
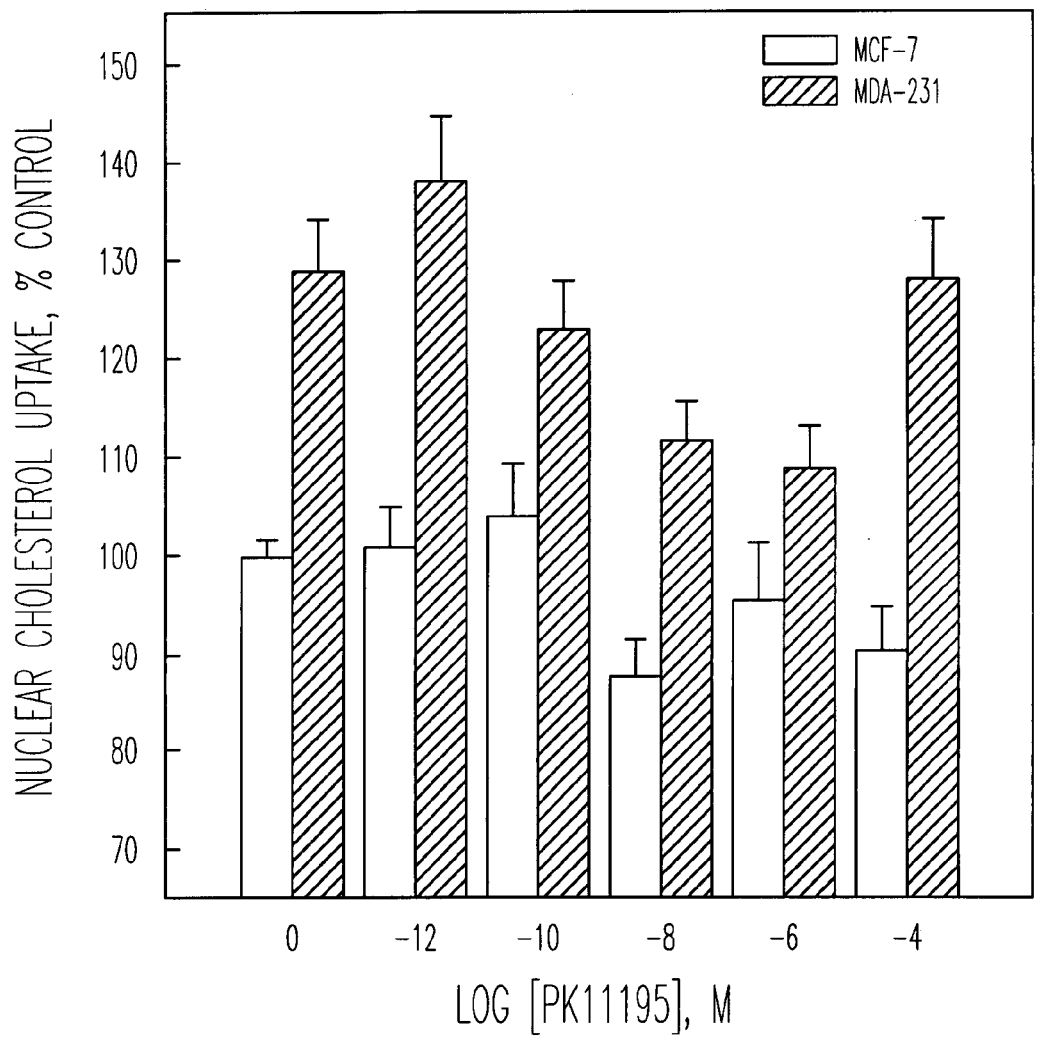
FIG. 6 represents cholesterol uptake by MDA-231 and MCF-7 nuclei. Uptake of [$^3$H] cholesterol by nuclei isolated from MDA-231 and MCF-7 cells was measured in response to varying doses of PK11195. Data is expressed as % cholesterol uptake into MCF-7 nuclei in the absence of any PK11195. Data points represent the mean±S. E. of five (MDA-231) or four (MCF-7) independent experiments carried out in quadruplicate.

Previous studies from this laboratory have shown that PBR plays a key role in steroidogenesis by mediating the translocation of cholesterol from the outer mitochondrial membrane to the inner mitochondrial membrane (Krueger and Papadopoulos, 1990, supra). More recently, we have shown that PBR mediates cholesterol uptake even in non-mitochondrial membranes (Papadopoulos et al., 1997, supra). To test whether or not PBR may play a similar role in MDA-231 nuclear membranes, intact nuclei were isolated from both MDA-231 and MCF-7 cells. Isolated nuclei were incubated with 100 nM [$^3$H] cholesterol in the absence or presence of increasing concentrations of PK11195 (FIG. 6). MDA-231 nuclei demonstrated the ability to uptake 30% more cholesterol relative to MCF-7 nuclei. In MDA-231 nuclei, -8 to -6M PK11195 resulted in roughly a 20% decrease in the amount of cholesterol uptake, levels comparable to both stimulated and unstimulated MCF-7 cholesterol uptake. MCF-7 nuclei failed to respond to the PK11195 dose-response (FIG. 6).

Figure 7:
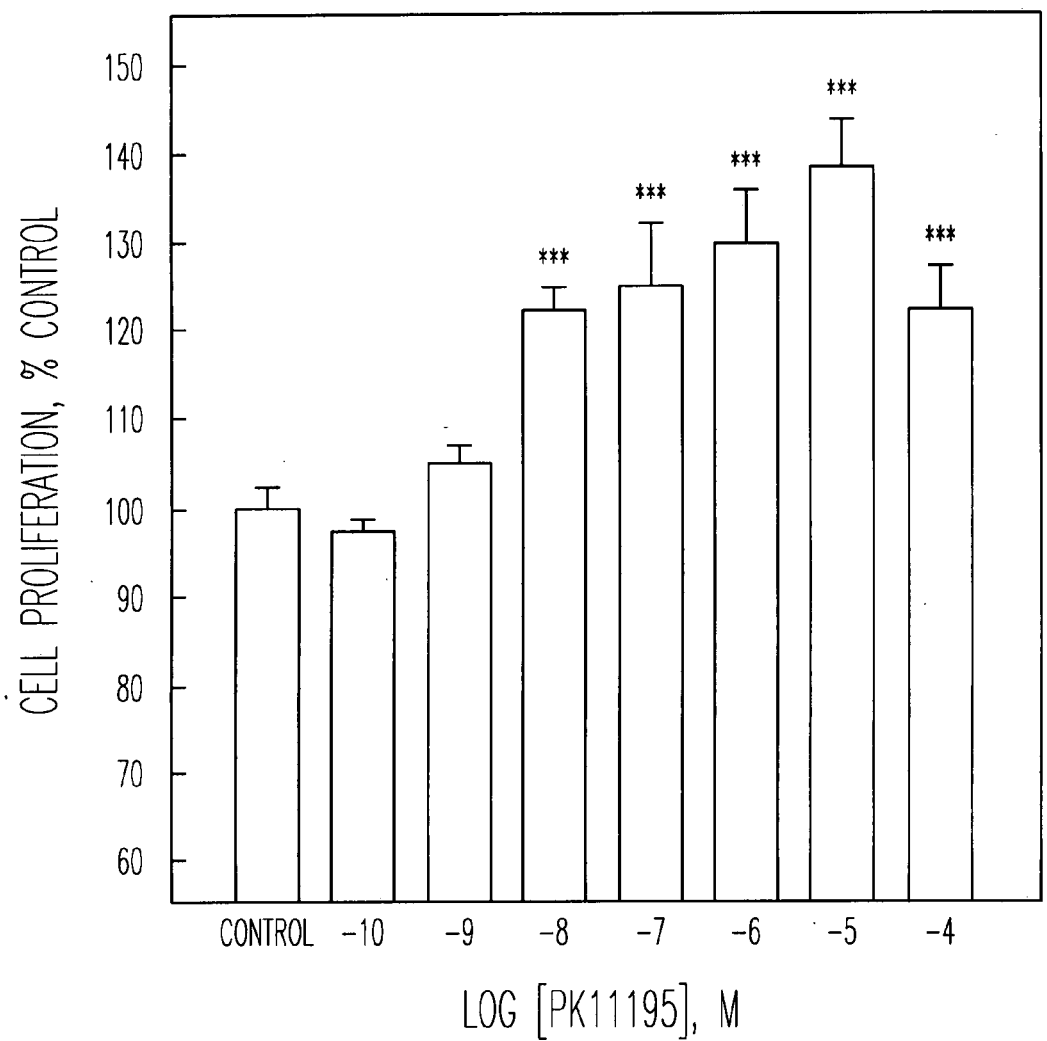
FIG. 7 demonstrates the effect of PK11195 on MDA-231 cell proliferation. MDA-231 cells grown in 96-well plates were washed with PBS and cultured in media supplemented with 0.1% FBS 24 h prior to any treatment. The indicated concentrations of PK11195 were added to the cells cultured in DMEM supplemented with 0.1% FBS and incubated for 24 h at 37° C. 4 h prior to the end of incubation, bromodeoxyuridine (BrdU) was added to each well. Incorporation of BrdU was measured at 450 nm (reference=700 nm). Data points represent the mean±S.E. of three independent experiments carried out in quadruplicate. ***, $p<0.05$.

Numerous studies performed in the early 1980's showed that Ro5-4864 and PK11195, specific PBR ligands, regulate cell proliferation in a number of cancer models [Clarke and Ryan (1980) *Nature* 287: 160-161; Wang (1984) *PNAS U.S.A.* 81:753-756; Laird (1989) *Eur. J. Pharm.* 171:25-35; Ikezaki and Black (1990) *Cancer Letters* 49:115-120; Bruce (1991) *Brain Res.* 564:167-170; Garnier et al. (1993) *Endocrinology* 132:444-458; Camins (1995) *Eur. J. Phar.* 272: 289-292; Neary (1995) *Brain Research* 675:27-30). Using the Bromodeoxyuridine (BrdU) Cell Proliferation ELISA (Boehringer-Mannheim, Indianapolis, Ind.), we examined the effects of PK11195 on MDA-231 cell proliferation (FIG. 7). After 24 h, low nanomolar PK11195 (–10 and –9M) showed no effect on MDA-231 cell proliferation. However, –8M PK11195 stimulated MDA-231 cell proliferation between 20% to 25%, an increase similar to earlier reports (Ikezaki and Black, 1990, supra). Stimulation of MDA-231 cell proliferation was maximal (40%) at –5M PK11195. After 48 h, the dose-response curve shifted to the left (data not shown). Cell proliferation was stimulated 40% by –8M PK 11195, although no stimulation was seen at any of the micromolar concentrations.

EXAMPLE 3

Figure 8:
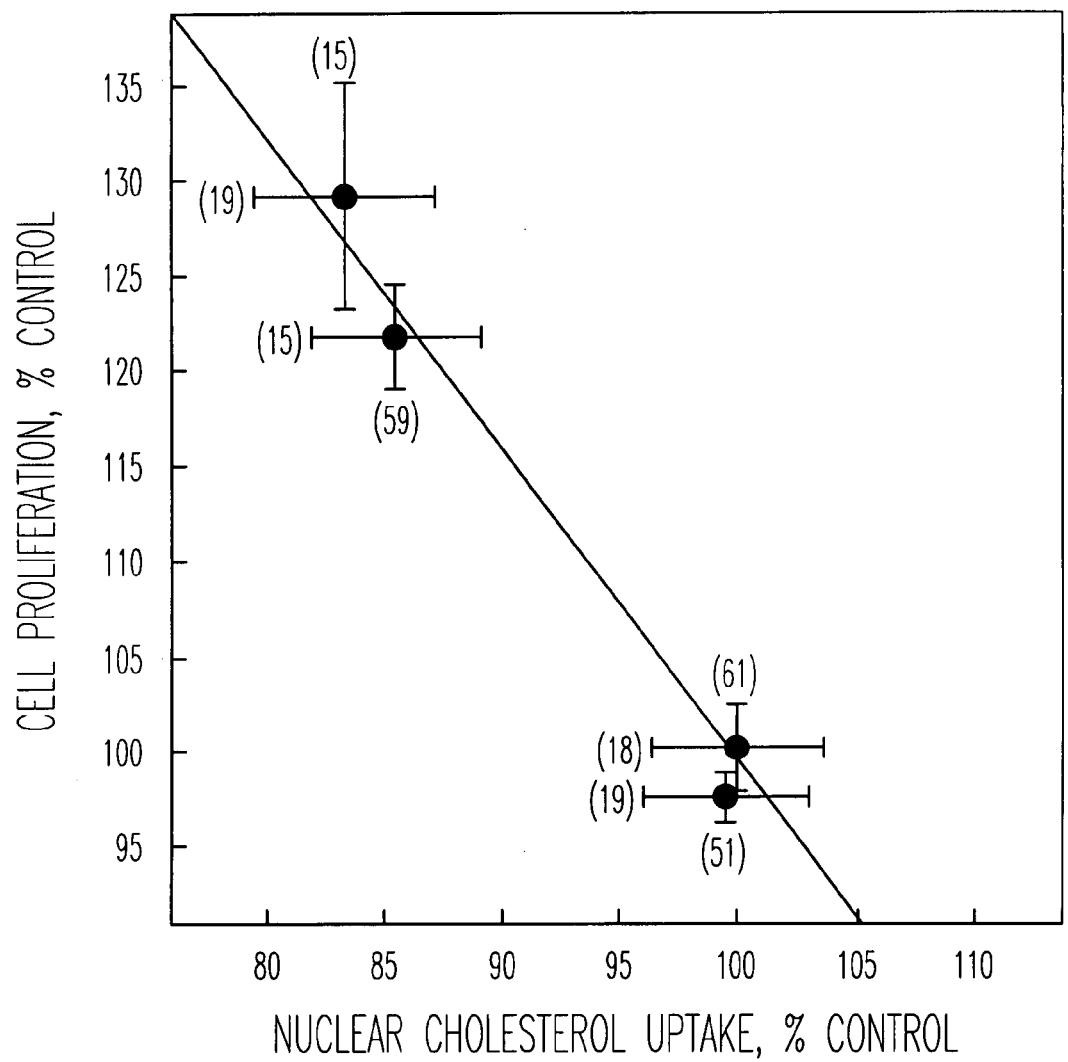
FIG. 8 shows PBR mediated nuclear cholesterol uptake correlates with the proliferation rate of MDA-231 cells. The means of all data points for 0, 10-10, 10-8, and 10-6 M PK11195 from the previously described cell proliferation assay were plotted against the corresponding means from the previously described cholesterol uptake assay. A regression line drawn for all plotted data gives a coefficient of correlation of 0.99. Numeric values in (n) indicate the number data points taken for each mean±S. E.

A Decrease in Cholesterol Uptake Into MDA-231 Nuclei Correlates With an Increase in Cell Proliferation We have shown that PK11195 inhibits the uptake of cholesterol into the nucleus at nanomolar and low micromolar concentrations. We have also shown that PK11195 also stimulates cell proliferation at these concentrations. We were then interested in determining whether or not the regulation of nuclear cholesterol uptake correlates with the PBR-mediated regulation of cell proliferation. In order to determine such a relationship, all of the cholesterol data for given concentrations of PK11195 was plotted against all of the proliferation data at the same PK11195 concentrations. A regression line for all points gave a coefficient of correlation (r) of 0.75. Considering that –4M PK11195 is a toxic concentration, removal of the data from –4M PK11195 yields a coefficient of correlation (r) of 0.99 (FIG. 8).

EXAMPLE 4

MDA-231 Cells Express DBI, the Endogenous PBR Ligand

Given the ability of exogenous PBR ligands to regulate nuclear cholesterol uptake and cell proliferation in MDA- 231 cells, we then examined whether or not MDA-231 cells express the endogenous PBR ligand the polypeptide diazepam binding inhibitor (DBI). The presence of DBI in an aggressive human breast cancer cell line would give support to the hypothesis that PBR is involved in the advancement of human breast cancer. Indeed, immunocytochemistry of MDA-231 cells with anti-DBI antiserum reveals that this cell line possesses cytoplasmic DBI (data not shown).

EXAMPLE 5

Localization of PBR in Human Breast Tissue Biopsies From Normal Tissue

Figure 9A:
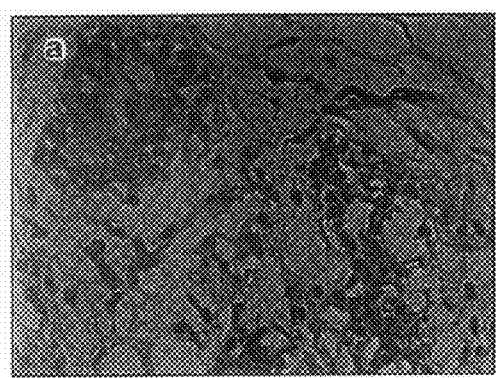
FIG. 9 shows PBR expression in normal human breast tissue. Paraffin embedded sections of normal breast tissue were immunostained with an anti-PBR antiserum at 1:500 dilution and counterstained with hematoxylin as previously described [Oke, B. O. et al. (1992) *Mol. Cell. Endocr*. 87:R1-R6; Garnier, M. et al. (1993) *Endocrinology* 132:444-458].
Figure 9B:
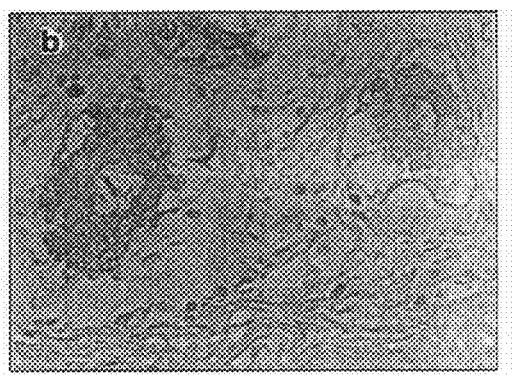
Figure 9C:
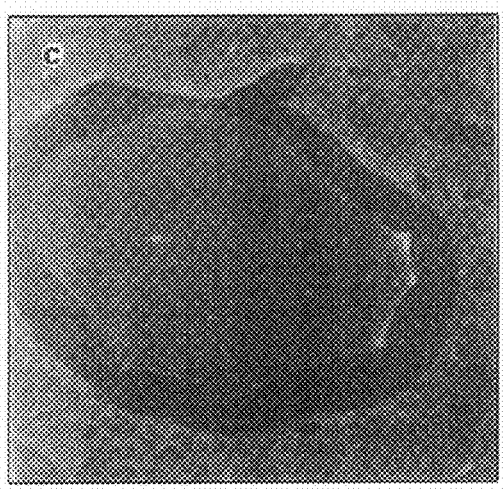
Figure 9D:
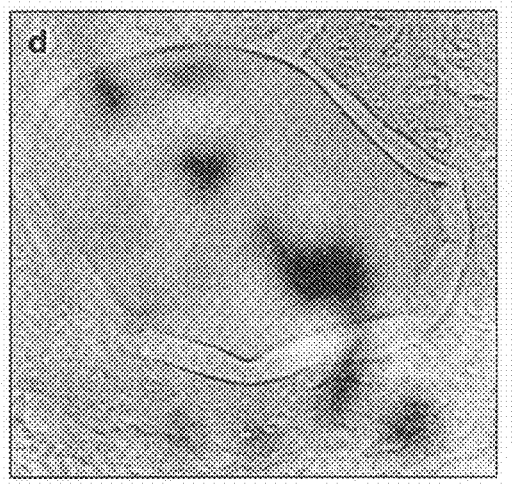
Figure 9E:
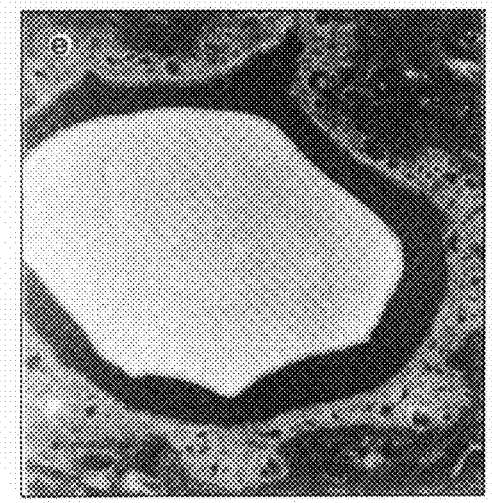
Figure 9F:
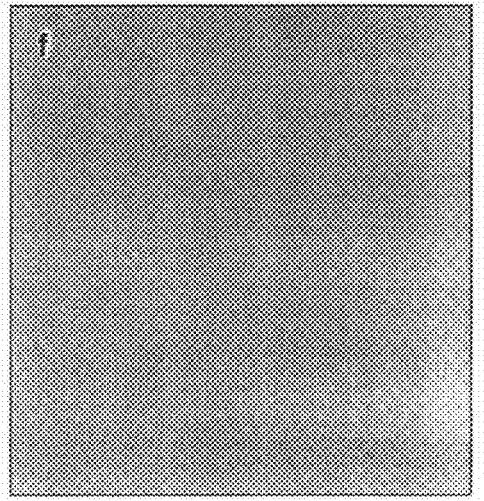

Paraffin embedded sections of normal breast tissue were immunostained with an anti-PBR antiserum at 1:500 dilution and counterstained with hematoxylin as previously described [Oke, B. O. et al. (1992) *Mol. Cel. Endocr.* 87: R1-R6; Garnier, 1993, supra]. Please note the distinct localization of PBR in the cytoplasm of the epithelial cells of normal human breast ducts (a). Obviously there is a low level of expression of PBR. In some samples, the hematoxylin counterstaining was omitted in order to examine whether the nucleus of the cells contained immunoreactive PBR protein (b). FIG. 9c shows also the localization of PBR in normal breast tissue cells. In this experiment an FITC-coupled secondary antibody was used to localize the immunoreactive PBR protein. FIG. 9d shows the phase contrast of the same tissue area. PBR ligand binding activity was determined using the fluorescent PBR derivative compound 4 [Munson, 1980, supra] (FIG. 9e). Ligand binding activity could be detected in the cytoplasm of the cells and at low levels, in agreement with the protein localization studies. Use of 1000 fold excess of the competitive ligand PK 11195 completely displaced the fluorescence, demonstrating the specificity of the labeling.

EXAMPLE 6

Figure 10A:
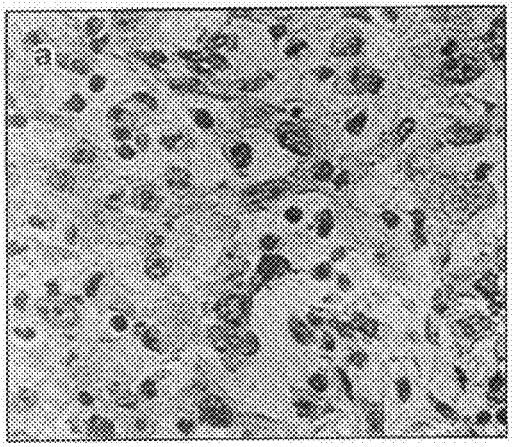
Figure 10B:
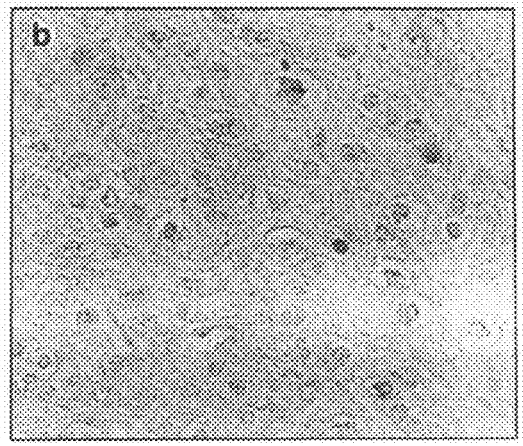
Figure 10C:
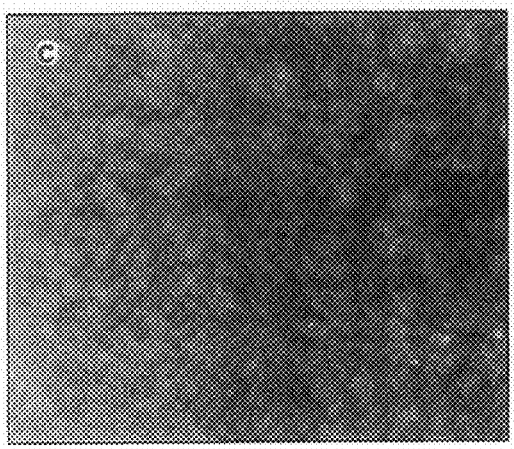
Figure 10D:
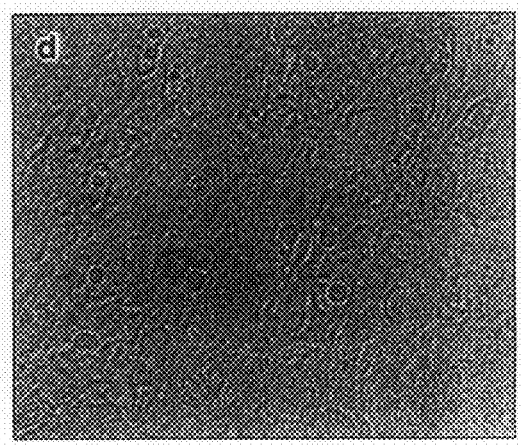
Figure 10E:
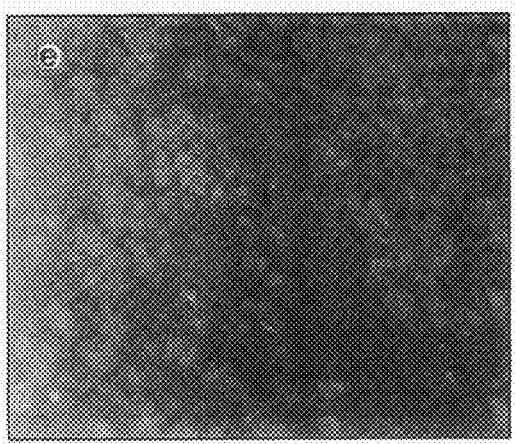
Figure 10F:
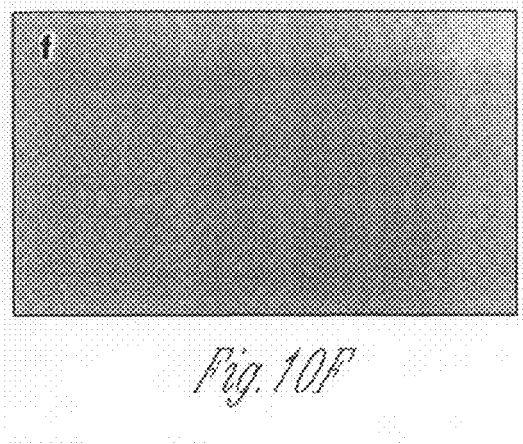

Nuclear Localization of High Levels of PBR in Human Breast Tissue Biopsies From Invasive/Metastatic Carcinomas Histologically breast carcinomas are classified into ductal and lobular types. Each type is further divided into in situ, invasive and aggressive these being the metastatic form of the cancer. All biopsies were obtained from the Lombardi Cancer Center at Georgetown University Medical Center. Biopsies were histologically characterized by the pathologist. In order to determine whether the results obtained using the invasive and aggressive human breast cancer cell lines are not an artifact of the cell culture system we used biopsies from in situ, invasive and aggressive breast carcinomas. FIG. 10 shows PBR expression and localization in aggressive carcinomas. Please note the distinct localization of PBR in the nucleus and the perinuclear area of the aggressive tumor cells (a). In some samples, the hematoxylin counterstaining was omitted in order to confirm the PBR positive staining of the nuclei of breast carcinoma cells (b). FIG. 11c also shows the localization of PBR in normal breast tissue cells. In this experiment an FITC-coupled secondary antibody was used to localize the immunoreactive PBR protein. A strong nuclear immunostaining could be observed. FIG. 10d shows the phase contrast of the same tissue area. PBR ligand binding activity was also determined in the aggressive breast carcinomas using the fluorescent PBR derivative compound 4 (FIG. 10e). Strong ligand binding activity could be detected in the nucleus of the cells, in agreement with the protein localization studies. Use of 1000 fold excess of the competitive ligand PK 11195 completely displaced the fluorescence, demonstrating the specificity of the labeling.

It should be noted that data from in situ and invasive breast carcinoma closely resembles the data obtained using the normal breast tissue. These findings clearly indicate that increase expression of PBR and nuclear localization is a characteristic of the aggressive phenotype of the tumor. Invasive breast tumors invade and grow locally but they do not metastasize. However, the aggressive tumors have the ability to invade and metastasize through the blood vessels to different places of the human body. Tumor metastasis into vital organs (such as lungs) is the most common cause of death.

EXAMPLE 7

Inhibition of PBR Expression Results in Reduced Rate of Cell Proliferation of Tumor Cells To evaluate the role of PBR in cell function, we developed a molecular approach based on the disruption of PBR gene, by homologous recombination, in the constitutive steroid producing R2C rat Leydig tumor cell line [Papadopoulos, V. et al. (1997) *J. Biol. Chem.* 272:32129-32135]. Inactivation of one allele of the PBR gene resulted in the suppression of PBR mRNA and ligand binding expression. Immunoblot and electron expression of PBR and nuclear localization is a characteristic of the aggressive phenotype of the tumor. Invasive breast tumors invade and grow locally but they do not metastasize microscopic immunogold labeling analyses confirmed the absence of the 18 kDa PBR protein in the selected mutant clones. The rate of cell proliferation was determined using the MTT proliferation assay (Boehringer Mannheim). FIG. 11 clearly shows that the rate of cell proliferation in the PBR mutant cell was reduced compared to the wild type cell suggesting a role of the receptor in cell proliferation.

DISCUSSION

In this report, we examined the role of PBR in human breast cancer through a model system comprising a series of human breast cancer cell lines. Through the course of this study we describe a strong correlation between the expression of PBR ligand binding activity and the invasive and chemotactic potential, as well as the expression of the breast cancer marker CD44, among the cell lines. Further, we show that PBR is differentially localized between highly aggressive and non-aggressive cell lines. Characterization of breast cancer PBR reveals that it is similar to the PBR studied in other human tissues with the exception of several point mutations that lead to the replacement of an alanine residue at position 147 with a threonine residue and a replacement of histidine 162 with arginine. Functionally, we find that PBR is responsible for the increased uptake of cholesterol by the nuclei of a highly aggressive cell line, MDA-231, relative to a non-aggressive cell line, MCF-7. Also, we find that PBR regulates cell proliferation of MDA-231 and, moreover, that this regulation is strongly linked to the ability of PBR to regulate cholesterol uptake into MDA-231 nuclei. The fact that nanomolar and low micromolar concentrations, and not high micromolar concentrations, of PK11195 are responsible for both of these actions indicates that these events are the result of specific interactions, of the drugs used, with PBR and not some non-specific activity of the ligand.

The expression of PBR protein levels in the model system studied in this paper mirrors that seen in other human cancer studies. Cornu et al (1992, *Acta Neurochir.* 119:146-152) have shown that PBR site densities are as much as 12-fold higher in high grade astrocytomas and glioblastomas relative to normal brain tissue. A study by Miettinen et al (1995, supra) also indicates that PBR is highly upregulated in high grade human astrocytic tumors relative to low grade tumors. Further, a Positron Emission Tomography study by Pappata et al (1991, *J. Nuclear Med.* 32:1608-1610) revealed that binding of PK11195, the PBR-specific ligand utilized throughout the current study, is two-fold greater in glioblastomas than in normal human gray matter. Our data supports these previous studies by showing that PBR binding in MDA-231 cells is approximately seven-fold higher than the mildly aggressive ADR cell line and infinitely greater than in the non-aggressive MCF-7 cell line.

At the transcriptional level, however, this correlation does not appear to be as tight. While MDA-231 cells express 17 to 20-fold higher PBR cDNA than MCF-7 cells, PBR cDNA expression is almost 1.5-fold greater in the ADR cell line compared to MDA-231 cells. This result appears to be anomalous, however, considering that ADR cells apparently localize PBR to the cytoplasm and the nuclear envelope, it may represent a transition phase between the non-aggressive state to a more aggressive state in the context of the battery of human breast cancer cell lines examined in this paper. It is difficult to rectify, however, because little is known about the regulation of PBR expression.

Partial sequence analysis revealed that a point mutation in both MDA-231 and MCF-7 cells results in the replacement of alanine 147 with a threonine residue. Molecular modeling of the receptor indicates that this residue lies within the cholesterol pore region of the receptor (Papadopoulos, 1997, supra). Currently, it is not apparent whether or not this mutation has a resulting phenotype. It appears that it does not alter the ability of cholesterol to move through the pore since cholesterol is incorporated into MDA-231 nuclei. The fact that it is present in both the MDA-231, a highly aggressive breast cancer cell line, and in MCF-7, a non-aggressive cell line, indicates that this mutation may represent an early event in the progression of this disease.

PBR is primarily targeted to the outer mitochondrial membrane in tissues in which it is expressed in great abundance (Papadopoulos, 1993, supra). It has also been found, however, in other cellular organelles such as the plasma membrane as well as the peroxisome [Papadopoulos, 1993, supra; Woods et al. (1996) *Biochemical Pharmacol.* 51: 1283-1292]. The lack of a distinct mitochondrial target sequence and the largely hydrophobic nature of PBR makes it feasible that PBR could exist in a variety of membranes. Differential localization of PBR may also be possible through the existence of chaperone proteins and PBR-associated proteins that may direct PBR to the membranes of specific organelles and may influence PBR's functioning [Papadopoulos, V. (1998) *Proc. Exp. Biol. Med.*217: 130-142]. The significance of such differential localization, however, has not been investigated and is currently unknown. It will be necessary to distinguish whether the nuclear localization of PBR in MDA-231 cells is the result of a specific amino acid sequence present in the yet undetermined amino-terminus of the protein or the shuttling of PBR to the nucleus via association with another protein.

The data presented in this application suggests that nuclear PBR is responsible for regulating movement of cholesterol into the nuclear membrane and that this regulation is related to its modulation of cell proliferation. Cholesterol is a major lipid component of every membrane and has been suggested to play a role in the advancement of a variety of pathologies including breast cancer [Coleman et al. (1997) In: *Cholesterol: Its Functions and Metabolism in Biology and Medicine*. R. Bittman (Ed.). Plenum Press, New York, pp. 363-435; Kokogleu et al. (1994) *Cancer Letters* 82: 175-178]. Further, reports on animal dietary, cellular, and enzyme-specific studies implicate a role for cellular cholesterol in the regulation of cell proliferation (Coleman, 1997, supra). Cholesterol has been shown to tightly regulate the activity of the sterol regulatory element binding proteins (SREBP) found in the nuclear membrane and the endoplasmic reticulum [Brown and Goldstein, 1997) *Cell* 89:331-340]. In the presence of excessive cholesterol, premature SREBP is not fully cleaved and, therefore, the mature form is not released and cannot enter the nucleus to carry out transcription (Brown and Goldstein, 1997, supra). SREBPs are responsible for the transcriptional regulation of the enzymes involved in the cholesterol biosynthetic pathway as well as the enzymes involved in fatty acid synthesis and uptake (Brown and Goldstein, 1997, supra). One possible outcome of concentrating cellular cholesterol to the nuclear membrane may be to inhibit the activation of nuclear membrane SREBPs. With the tight correlation between nuclear uptake of cholesterol in MDA-231 and PBR's regulation of MDA-231 cell proliferation, the SREBP pathway may shed some light as to how PBR is regulating cell proliferation in these cells and should be the target of future research in this area.

It is distinctly possible that the correlation between PBR expression and aggressive phenotype, as well as the nuclear localization of PBR in a highly aggressive breast cancer cell line, may be due to the overall differential metabolism and cellular activity between the cell lines studied. The functionality of PBR in the MDA-231 cell line, namely the ability to regulate both nuclear cholesterol uptake and cell proliferation, as well as the strong correlation between these two seemingly separate events, suggests that indeed PBR is playing a role in the progression of breast malignancies. The presence of the putative endogenous PBR ligand, DBI in the cytoplasm of MDA-231 cells further suggests the likelihood that PBR is fully functional in these cells.

Malignant breast tumors are primarily characterized by aberrant cell proliferation, tumor invasion and metastasis. Several molecular and cellular mechanisms have been proposed to account for these phenomena and a number of prognostic indicators have been identified. While these markers have been useful in helping clinicians develop prognoses, they have failed to provide adequate enough information about the mechanisms responsible for tumor malignancy so that effective anti-cancer therapies may be developed. Given the data presented in this report, we believe that PBR is a major component of the progression of breast cancer. While a great deal more needs to be learned about PBR and its ability to regulate cell proliferation and cholesterol movement, we believe it is a major step in understanding this disease. Our data as well as previous studies implies that PBR may serve well as a prognostic marker indicating that higher levels of PBR in cancerous tissues implying advancement of disease. Further, a great number of PBR ligands are known, including benzodiazepines and isoquinoline carboxamides, whose PBR-binding and pharmacological characteristics are well documented. Many of these ligands have been shown to act either agonists or as antagonists to PBR action and may be potential targets for anti-cancer therapies. In addition, the availability of radiolabeled and fluorescent ligands may be useful in the diagnosis and prognosis of the disease.

What is claimed is:

1. An isolated nucleic acid consisting of SEQ ID NO:1, SEQ ID NO:2, or the complete complement thereof.

2. An isolated nucleic acid that comprises a nucleotide sequence that is the complete complement of SEQ ID NO:1; wherein said nucleic acid, when introduced into a cell line that expresses a polynucleotide comprising SEQ ID NO:1 or which encodes a peripheral-type benzodiazepine receptor protein having a mutant threonine residue at position 147, inhibits the expression of the polynucleotide.

3. An isolated nucleic acid consisting of SEQ ID NO:1 or the complete compliment thereof.

4. An isolated nucleic acid comprising the complete complement of SEQ ID NO:1.

5. A composition comprising the isolated nucleic acid of claim 1.

6. The composition of claim 5, wherein the nucleic acid is present in a vector and is synthesized in a mammalian cell in vitro following introduction of said vector into said cell.

7. The composition of claim 6, wherein the nucleic acid is synthesized in a mammary gland cell in vitro following introduction of said vector into said mammary gland cell.

8. The nucleic acid of claim 2, which is comprised in a proteoliposome containing viral envelope receptor proteins.

9. The nucleic acid of claim 2, which is present in a vector.

10. The nucleic acid of claim 2, which is contained in a carrier.

11. The nucleic acid of claim 10 wherein said carrier is a protein selected from the group consisting of a cytokine or polylysine-glycoprotein carrier.

12. The nucleic acid of claim 2, which is comprised in a microbead.

13. The nucleic acid of claim 9, which is synthesized in a mammalian cell in vitro following introduction of said vector into said cell.

* * * * *